(12) United States Patent
Huisman et al.

(10) Patent No.: US 6,689,589 B2
(45) Date of Patent: *Feb. 10, 2004

(54) BIOLOGICAL SYSTEMS FOR MANUFACTURE OF POLYHYDROXYALKANOATE POLYMERS CONTAINING 4-HYDROXYACIDS

(75) Inventors: Gjalt W. Huisman, San Carlos, CA (US); Frank Skraly, Somerville, MA (US); David P. Martin, Arlington, MA (US); Oliver P. Peoples, Arlington, MA (US)

(73) Assignee: Metabolix, Inc., Cambridge, MA (US)

( * ) Notice: Subject to any disclaimer, the term of this patent is extended or adjusted under 35 U.S.C. 154(b) by 53 days.

This patent is subject to a terminal disclaimer.

(21) Appl. No.: 10/006,915

(22) Filed: Nov. 9, 2001

(65) Prior Publication Data

US 2002/0187530 A1 Dec. 12, 2002

Related U.S. Application Data

(63) Continuation of application No. 09/156,809, filed on Sep. 18, 1998, now Pat. No. 6,316,262.
(60) Provisional application No. 60/059,373, filed on Sep. 19, 1997.

(51) Int. Cl.$^7$ .......................... C12P 7/62; C12N 15/54; C12N 15/53
(52) U.S. Cl. .................. 435/135; 435/490; 435/252.33; 435/320.1
(58) Field of Search ........................ 435/490, 252.33, 435/320.1, 135

(56) References Cited

U.S. PATENT DOCUMENTS

| | | |
|---|---|---|
| 4,430,430 A | 2/1984 | Momose et al. |
| 4,876,331 A | 10/1989 | Doi |
| 5,245,023 A | 9/1993 | Peoples et al. |
| 5,250,430 A | 10/1993 | Peoples et al. |
| 5,286,842 A | 2/1994 | Kimura |
| 5,292,860 A | 3/1994 | Shiotani et al. |
| 5,378,616 A | 1/1995 | Tujimoto et al. |
| 5,461,139 A | 10/1995 | Gonda et al. |
| 5,502,273 A | 3/1996 | Bright et al. |
| 5,516,883 A | 5/1996 | Hori et al. |
| 5,534,432 A | 7/1996 | Peoples et al. |
| 5,563,239 A | 10/1996 | Hubbs et al. |
| 5,602,321 A | 2/1997 | John |
| 5,610,041 A | 3/1997 | Somerville et al. |
| 5,650,555 A | 7/1997 | Somerville et al. |
| 5,663,063 A | 9/1997 | Peoples et al. |
| 6,117,658 A | 9/2000 | Dennis et al. |

FOREIGN PATENT DOCUMENTS

| | | |
|---|---|---|
| CA | 2006508 | 3/1996 |
| WO | WO 91/00917 | 1/1991 |
| WO | WO 93/02187 | 7/1992 |
| WO | WO 93/02194 | 7/1992 |
| WO | WO 92/19747 | 11/1992 |
| WO | WO 93/06225 | 4/1993 |
| WO | WO 94/11519 | 5/1994 |
| WO | WO 94/12014 | 6/1994 |
| WO | WO 95/20614 | 11/1994 |
| WO | WO 95/20615 | 8/1995 |
| WO | WO 96/20621 | 7/1996 |

OTHER PUBLICATIONS

Abe, et al., "Biosynthesis from gluconate of a random copolyester consisting of 3–hydroxybutyrate and medium–chain–length 3–hydroxyalkanoates by Pseudomonas sp. 61–3.," *Int. J. Biol. Macromol.* 16:115–119 (1994).

Aidoo, et al., "Cloning, sequencing and disruption of a gene from *Streptomyces clavuligerus* involved in clavulanic acid biosynthesis," *Gene* 147:41 (1994).

Allen, et al., "DNA sequence of the putA gene from *Salmonella typhimurium*: a bifunctional membrane–associated dehydrogenase that binds DNA," *Nucleic Acids Res.* 21:1676 (1993).

Amarasingham & Davis, "Regulation of alpha–ketoglutarate dehydrogenase formation in *Escherichia coli*," *J. Biol. Chem.* 240: 3664–3668 (1965).

Amos & McInerey, "Composition of poly–β–hydroxyalkanoate from *Syntrophomonas wolfei* grown on unsaturated fatty acid substrates," *Arch. Microbiol.* 155–103–06 (1991).

Amuro, et al., "Isolation and characterization of the two distinct genes for human glutamate dehydrogenase," *Biochem. Biophys. Acta* 1049: 216–218 (1990).

André and Jauniaux, "Nucleotide sequence of the yeast UGA1 gene encoding GABA transaminase," *Nucl. Acid Res.* 18:3049 (1990).

Bartsch, et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172:7035–7042 (1990).

Baum, et al., "A plant glutamate decarboxylase containing a calmodulin binding domain. Cloning, sequence, and functional analysis," *J. Biol. Chem.* 268:19610–19617 (1993).

(List continued on next page.)

*Primary Examiner*—Charles L. Patterson, Jr.
(74) *Attorney, Agent, or Firm*—Holland & Knight LLP

(57) ABSTRACT

The gene encoding a 4-hydroxybutyryl-Co A transferase has been isolated from bacteria and integrated into the genome of bacteria also expressing a polyhydroxyalkanoate synthase, to yield an improved production process for 4HB-containing polyhydroxyalkanoates using transgenic organisms, including both bacteria and plants. The new pathways provide means for producing 4HB containing PHAs from cheap carbon sources such as sugars and fatty acids, in high yields, which are stable. Useful strains are obtaining by screening strains having integrated into their genomes a gene encoding a 4HB-CoA transferase and/or PHA synthase, for polymer production. Processes for polymer production use recombinant systems that can utilize cheap substrates. Systems are provided which can utilize amino acid degradation pathways, α-ketoglutarate, or succinate as substrate.

13 Claims, 14 Drawing Sheets

OTHER PUBLICATIONS

Bell and Malmberg, "Analysis of a cDNA encoding arginine decarboxylase from oat reveals similarity to the *Escherichia coli* arginine decarboxylase and evidence of protein processing," *Mol. Gen. Genet.* 224:431 (1990).

Benachenhou–Lahfa, et al., "PCR–mediated cloning and sequencing of the gene encoding glutamate dehydrogenase from the archaeon *Sulfolobus shibatae*: identification of putative amino–acid signatures for extremophilic adaptation," *Gene* 140: 17–24 (1994).

Blattner, et al., "The complete genome sequence of *Escherichia coli* K–12," *Science* 277:1453 (1997).

Botsford, et al., "Accumulation of glutamate by *Salmonella typhimurium* in response to osmotic stress," *Appl. Environ. Microbiol.* 60:2568 (1994).

Brandl, et al., "Ability of the phototrophic bacterium *Rhodospirillum rubrum* to produce various poly (beta–hydroxyalkanoates): potential sources for biodegradable polyesters," *Int. J. Biol. Macromol.* 11:49–55 (1989).

Bu, et al., "The exon–intron organization of the genes (GAD1 and GAD2) encoding two human glutamate decarboxylases (GAD67 and GAD65) suggests that they derive from a common ancestral GAD," *Genomics* 21:222–228 (1994).

Bult, et al., "Complete genome sequence of the methanogenic archaeon, *Methanococcus jannaschii*," *Science* 273:1058–1073 (1996).

Chang, et al., "Nucleotide Sequence of cDNA (Accession No. U63832) Encoding Arginine Decarboxylase from Carnation Flowers," *Plant Physiol.* 112–863 (1996).

Chavez, et al., "The NADP–glutamate dehydrogenase of the cyanobacterium Synechocystis 6803: cloning, transcriptional analysis and disruption of the gdhA gene," *Plant Mol. Biol.* 28:173–188 (1995).

Chen & Maloy, "Regulation of proline utilization in enteric bacteria: cloning and characterization of the Klebsiella put control region," *J. Bacteriol.* 173:783 (1991).

Cho, et al., "Identification of *Agrobacterium tumefaciens* genes that direct the complete catabolism of octopine," *J. Bacteriol.* 178:1872 (1996).

Chu, et al., "Enzymatically active truncated cat brain glutamate decarboxylase: expression, purification, and absorption spectrum," *Arch. Biochem. Biophys.* 313:287–295 (1994).

Cock, et al., "A nuclear gene with many introns encoding ammonium–inducible chloroplastic NADP–specific glutamate dehydrogenase(s) in *Chlorella sorokiniana*," *Plant Mol. Biol.* 17:1023–144 (1991).

Cogoni, et al., "*Saccharomyces cerevisiae* has a single glutamate synthase gene coding for a plant–like high–molecular–weight polypeptide," *J. Bacteriol.* 177:792 (1995).

Cole, et al., "Deciphering the biology of *Mycobacterium tuberculosis* from the complete genome sequence," *Nature* 393:537 (1998).

Deckert, et al., "The complete genome of the hyperthermophilic bacterium *Aquifex aeolicus*," *Nature* 392:353 (1998).

Delauney & Verma, "A soybean gene encoding delta 1–pyrroline–5–carboxylate reductase was isolated by functional complementation in *Escherichia coli* and is found to be osmoregulated," *Mol. Gen. Genet.* 221:299 (1990).

Desmet, et al., "Characterization of intracellular inclusions formed by *Pseudomonas oleovorans* during growth on octane," *J. Bacteriol.* 154:870–878 (1983).

Diruggiero, et al., "Expression and in vitro assembly of recombinant glutamate dehydrogenase from the hyperthermophilic archaeon *Pyrococcus furiosus*," *Appl. Environ. Microbiol.* 61:159–164 (1995).

Doi, "Microbial Synthesis, Physical Properties, and Biodegradability of Polyhydroxyalkanoates," *Macromol. Symp.* 98:585–599 (1995).

Doi, et al., "Biosynthesis and characterization of poly(3–hydroxybutyrate–co–4–hydroxybutyrate) in *Alcaligenes eutrophus*," *Int. J. Biol. Macromol.* 12: 106 (1990).

Doi, et al., "Nuclear Magnetic Resonance Studies on Unusual Bacterial Copolyesters of 3–Hydroxybutyrate and 4–Hydroxybutyrate," *Macromolecules* 21:2722–2727 (1988).

Duncan, et al., "Purification and properties of NADP–dependent glutamate dehydrogenase from *Ruminococcus flavefaciens* FD–1," *Appl. Environ. Microbiol.* 58:4032–4037 (1992).

Eggen, et al., "The glutamate dehydrogenase–encoding gene of the hyperthermophilic archaeon *Pyrococcus furiosus*: sequence, transcription and analysis of the deduced amino acid sequence," *Gene* 132:143–148 (1993).

Filetici, et al., "Sequence of the GLT1 gene from *Saccharomyces cerevisiae* reveals the domain structure of yeast glutamate synthase," *Yeast* 12:1359 (1996).

Fleischmann, et al., "Whole–genome random sequencing and assembly of *Haemophilus influenzae* Rd," *Science* 269:496 (1995).

Gallego, et al., "A role for glutamate decarboxylase during tomato ripening: the characterisation of a cDNA encoding a putative glutamate decarboxylase with a calmodulin–binding site," *Plant Mol. Bio.* 27:1143–1151 (1995).

Galloway, et al., "Phylogenetic utility of the nuclear gene decarboxylase: an example from Brassicaceae," *Mol Biol Evol.* 15(10):1312–20 (1998).

Gasser & Fraley, "Genetically Engineering Plants for Crop Improvement," *Science* 244:1293–1299 (1989).

Gerngross, et al., "Enzyme–catalyzed synthesis of poly [(R)–(–)–3–hydroxybutyrate]: formation of macroscopic granules in vitro," *Proc. Natl. Acad. Sci. USA* 92:6279 (1995).

Gerngross, et al., "Overexpression and purification of the soluble polyhydroxyalkanoate synthase from *Alcaligenes eutrophus*: evidence for a required posttranslational modification for catalytic activity," *Biochemistry* 33:9311 (1994).

Gonzáles, et al., "Cloning of a yeast gene coding for the glutamate synthase small subunit (GUS2) by complementation of *Saccharomyces cerevisiae* and *Escherichia coli* glutamate auxotrophs," *Mol. Microbiol.* 6:301–308 (1992).

Gregerson, et al., "Molecular characterization of NADH–dependent glutamate synthase from alfalfa nodules," *Plant Cell* 5:215 (1993).

Hein, et al., "Biosynthesis of poly(4–hydroxybutyric acid) by recombinant strains of *Escherichia coli*," *FEMS Microbiol. Lett.* 153:411–418 (1997).

Herrero, et al., "Transposon vectors containing non–antibiotic resistance selection markers for cloning and stable chromosomal insertion of foreign genes in gram–negative bacteria," *J. Bacteriol.* 172:6557–6567 (1990).

Hiramitsu, et al., "Production of Poly(3–hydroxybutyrate–co–4–hydroxybutyrate) by *Alcaligenes Latus*," *Biotechnol. Lett.* 15:461 (1993).

Jesudason & Marchessault, "Synthetic Poly[(R, S)–β–hydroxyalkanoates] with Butyl and Hexyl Side Chains," *Macromolecules* 27:2595–602 (1994).

Jimenez–Zurdo, et al., "The *Rhizobium meliloti* putA gene: its role in the establishment of the symbiotic interaction with alfalfa," *Mol. Microbiol.* 23:85 (1997).

Johnston, et al., "Complete nucleotide sequence of *Saccharomyces cerevisiae* chromosome VIII," *Science* 265:2077 (1994).

Kaneko, et al., "Sequence analysis of the genome of the unicellular cyanobacterium Synechocystis sp. strain PCC6803. II. Sequence determination of the entire genome and assignment of potential protein–coding regions," *DNA Res.* 3:109 (1996).

Kato, et al., "Open reading frame 3 of the barotolerant bacterium strain DSS12 is complementary with cydD in *Escherichia coli:* cydD functions are required for cell stability at high pressure," *J. Biochem.* 120:301 (1996).

Kato, et al., "Production of a novel copolyester of 3–hydroxybutyric acid with medium–chain–length 3–hydroxyalkanoic acids by Pseudomonas sp. 61–3 from sugars, " *Appl. Microbiol. Biotechnol.* 45:363–70 (1996).

Keuntje, et al., "Expression of the putA gene encoding proline dehydrogenase from *Rhodobacter capsulatus* is independent of NtrC regulation but requires an Lrp–like activator protein," *J. Bacteriol.* 177:6432 (1995).

Kimura, et al., "Production of Poly(3–hydroxybutyrate–co–4–hydroxybutyrate) by *Pseudomonas Acidovorans,*" *Biotechnol. Lett.* 14:445 (1992).

Kinnaird, et al., "The complete nucleotide sequence of the *Neurospora crassa*am (NADP–specific glutamate dehydrogenase) gene," *Gene* 26:253–260 (1983).

Kirby, et al., "Purification and properties of rabbit brain and liver 4–aminobutyrate aminotransferases isolated by monoclonal–antibody immunoadsorbent chromatography," *Biochem. J.* 230:481–488 (1985).

Klenk, et al., "The complete genome sequence of the hyperthermophilic, sulphate–reducing archaeon *Archaeoglobus fulgidus,*" *Nature* 390:364 (1997).

Kunioka, et al., "New bacterial copolyesters produced in *Alcaligenes eutrophus* from organic acids," *Polym. Commun.* 29:174 (1988).

Kwon, et al., "Brain 4–aminobutyrate aminotransferase. Isolation and sequence of a cDNA encoding the enzyme," *J. Biol. Chem.* 267:7215–7216 (1992).

Lageveen, et al., "Formation of Polyesters by *Pseudomonas oleovorans*: Effect of Substrates on Formation and Composition of Poly–(R)–3–Hydroxyalkanoates and Poly–(R)–3–Hydroxyalkenoates," *Appl. Environ. Microbiol.* 54:2924–2932 (1988).

Lee, et al., "Biosynthesis of copolyesters consisting of 3–hydroxybutyric acid and medium–chain–length 3–hydroxyalkanoic acids from 1,3–butanediol or from 3–hydroxybutryrate by *Pseudomonas sp.* A33," *Appl. Microbiol. Biotechnol.* 42: 901–909 (1995).

Lee, et al., "Enhanced biosynthesis of P(3HB–3HV) and P(3HB–4HB) by amplification of the cloned PHB biosynthesis genes in *Alcaligenes eutrophus,*" *Biotechnol. Lett.* 19: 771–774 (1997).

Lemoigne & Roukhelman, "Fermentation b–Hydroxybutyrique," *Annales des Fermentations* 5: 527–536 (1925).

Lin, et al., "Regulatory region with putA gene of proline dehydrogenase that links to the lum and the lux operons in *Photobacterium leiognathi,*" *Biochem. Biophys. Res. Commun.* 219:868 (1996).

Mandal & Ghosh, "Isolation of a glutamate synthase (GOGAT)–negative, pleiotropically N utilization –defective mutant of *Azospirillum brasilense:* cloning and partial characterization of GOGAT structural gene," *J. Bacteriol.* 175:8024 (1993).

Mat–Jan, et al., "Anaerobic growth defects resulting from gene fusions affecting succinyl–CoA synthetase in *Escherichia coli* K12," *Mol. Gen. Genet.* 215:276–280 (1989).

McBride, et al., "Controlled expression of plastid transgenes in plants based on a nuclear DNA–encoded and plastid–targeted T7 RNA polymerase," *Proc. Natl. Acad Sci. USA.* 91:7301–7305 (1994).

McFall & Newman, "Amino Acids as Carbon Sources," in *Escherichia coli and Salmonella,* (Neidhardt, ed.), pp. 358–379, ASM Press: Washington, D.C., 1996.

McLaggan, et al., "Interdependence of K+ and glutamate accumulation during osmotic adaption of *Escherichia coli,*" *J. Biol. Chem.* 269:1911 (1994).

Measures, "Role of amino acids in osmoregulation of non–halophilic bacteria," *Nature* 257:398 (1975).

Metzer and Halpern, "In vivo cloning and characterization of the gabCTDP gene cluster of *Escherichia coli* K–12," *Bacteriol.* 172: 3250–3256 (1990).

Miller, et al., "Cloning and characterization of gdhA, the structural gene for glutamate dehydrogenase of *Salmonella typhimurium,*" *J. Bacteriol.* 157:171–178 (1984).

Miyamoto, et al., "Possible physiological roles of aspartase, NAD– and NADP–requiring glutamate dehydrogenases of *Pseudomonas fluorescens,*" *J. Biochem.* 112:52–56 (1992).

Moore & Boyle, "Nucleotide sequence and analysis of the speA gene encoding biosynthetic arginine decarboxylase in *Escherichia coli,*" *J. Bacteriol.* 172:4631 (1990).

Morrissey, et al., "Partial cloning and characterization of an arginine decarboxylase in the kidney," *Kidney Int.* 47:1458 (1995).

Mountain, et al., "The *Klebsiella aerogenes* glutamate dehydrogenase (gdhA) gene: cloning, high–level expression and hybrid enzyme formation in *Escherichia coli,*" *Mol. gen. Genet.* 199:141–145 (1985).

Nagasu, et al., "Nucleotide Sequence of the GDH gene coding for the NADP–specific glutamate dehydrogenase of *Saccharomyces cerevisiae,*" *Gene* 37:247–253 (1984).

Nakamura, et al., "Cloning and sequencing of novel genes from *Vibrio alginolyticus* that support the growth of K+ uptake–deficient mutant of *Escherichia coli,*" *Biochim. Biophys. Acta* 1277:201 (1996).

Nam, et al., "Differential expression of ADC mRNA during development and upon acid stress in soybean (*Glycine max*) hypocotyls," *Plant Cell Physiol.* 38:1156 (1997).

Oliver, et al., "Determination of the nucleotide sequence for the glutamate synthase structural genes *Escherichia coli* K–12," *Gene* 60:1 (1987).

Owen & Pen, eds., *Transgenic Plants: A Production System for Industrial and Pharmaceutical Proteins* John Wiley & Sons Ltd: England, 1996.

Park, et al., "Isolation and characterization of recombinant mitochondrial 4–aminobutyrate aminotransferase," *J. Biol. Chem.* 268:7636–7639 (1993).

Pelanda, et al., "Glutamate synthase genes of the diazotroph *Azospirillum brasilense*. Cloning, sequencing, and analysis of functional domains," *J. Biol. Chem.* 268:3099 (1993).

Perez–Amador, et al., "Expression of arginine decarboxylase is induced during early fruit development and in young tissues of *Pisum sativum* (L)," *Plant Mol. Biol.* 28:997 (1995).

Perlak, et al., "Modification of the coding sequence enhances plant expression of insect control protein genes," *Proc. Natl. Acad. Sci. USA* 88: 3324 (1991).

Petit, et al., "PcrA is an essential DNA helicase of *Bacillus subtilis* fulfilling functions both in repair and rolling–circle replication," *Mol. Microbiol.* 29:261 (1998).

Poirier et al., "Polyhydroxybutyrate, a Biodegradable Thermoplastic Produced in Transgenic Plants," *Science* 256:520–523 (1992).

Presecan, et al., "The *Bacillus subtilis* genome from gerBC (311 degrees) to licR (334 degrees)," *Microbiology* 143:3313 (1997).

Rastogi, et al., "Cloning of tomato (*Lycopersicon esculentum* Mill.) arginine decarboxylase gene and its expression during fruit ripening," *Plant Physiol.* 103:829 (1993).

Redenbach, et al., A set of ordered cosmids and detailed genetic and physical map for the 8 Mb *Streptomyces coelicolor* A3(2) chromosome, *Mol. Microbiol.* 21:77 (1996).

Reitzer, "Ammonia Assimilation and the Biosyntheis of Glutamine, Glutamate, Aspartate, Asparagine, L–Alanine, and D–Alanine," *Escherichia coli and Salmonella*, (Neidhardt, ed.), pp. 391–407, ASM Press: Washington, D.C., 1996.

Saito & Doi, "Microbial synthesis and properties of poly(3–hydroxybutyrate–co–4–hydroxybutyrate) in *Comamonas acidovorans*," *Int. J. Biol. Macromol.* 16:99 (1994).

Saito, et al., "Microbial Synthesis and properties of poly(3–hydroxybutyrate–co–4–hydroxybutyrate)," *Polym. Int.* 39:169 (1996).

Sakakibara, et al., "Isolation and characterization of a cDNA that encodes maize glutamate dehydrogenase," *Plant Cell Physiol.* 36:789–797 (1995).

Savioz, et al., "Comparison of proC and other housekeeping genes of *Pseudomonas aeruginosa* with their counterparts in *Escherichia coli*," *Gene* 86:107 (1990).

Schaap, et al., "The *Agaricus bisporus* pruA gene encodes a cytosolic delta 1–pyrroline–5–carboxylate dehydrogenase which is expressed in fruit bodies but not in gill tissue," *Appl. Environ. Microbiol.* 63:57 (1997).

Scherf, et al., "Purification and properties of 4–hydroxybutyrate coenzyme A transferase from *Clostridium aminobutyricum*," *Appl. Environ. Microbiol.* 57:2699–2701 (1991).

Scherf, et al., "Succinate–ethanol fermentation in *Clostridium kluyveri*: purification and characterisation of 4–hydroxybutyryl–CoA dehydratase/vinylacetyl–CoA delta 3–delta 2–isomerase," *Arch. Microbiol.* 161:239–245 (1994).

Schleyer, et al., "Transient, specific and extremely rapid release of osmolytes from growing cells of *Escherichia coli* K–12 exposed to hypoosmotic shock," *Arch. Microbiol.* 160:424 (1993).

Shaibe, et al., "Control of Utilization of L–Arginine, L–Ornithine, Agmatine, and Putrescine as Nitrogen Sources in *Escherichia coli* K–12," *J. Bacteriol.* 163:938 (1995).

Smith, et al., "Complete genome sequence of *Methanobacterium thermoautotrophicum* deltaH: functional analysis and comparative genomics," *J. Bacteriol.* 179:7135 (1997).

Snedecor, et al., "Selection, expression, and nucleotide sequencing of the glutamate dehydrogenase gene of *Peptostreptococcus asaccharolyticus*," *J. Bacteriol.* 173:6162–6167 (1991).

Söhling & Gottschalk, "Molecular analysis of the anaerobic succinate degradation pathway in *Clostridium kluyveri*," *J. Bacteriol.* 178:871–880 (1996).

Söhling & Gottschalk, "Purification and characterization of a coenzyme–A–dependent succinate–semialdehyde dehydrogenase from *Clostridium kluyveri*," *Eur. J. Biochem.* 212: 121–127 (1993).

Sokhansandzh, et al., "Transfer of bacterial genes for proline synthesis in plants and their expression by various plant promotors," *Genetika* 33:906 (1997). (Abstract Only).

Steinbüchel and Valentin, "Diversity of bacterial polyhydroxyalkanoic acids," *FEMS Microbiol. Lett.* 128:219–28 (1995).

Steinbüchel and Wiese, et al., "A *Pseudomonas* strain accumulating polyesters of 3–hydroxybutyric acid and medium–chain–length 3–hydroxyalkanoic acids," *Appl. Microbiol. Biotechnol.* 37:691–97 (1992).

Stim & Bennett, "Nucleotide sequence of the *adi* gene, which encodes the biodegradative acid–induced arginine decarboxylase of *Escherichia coli*," *J. Bacteriol.* 175:1221 (1993).

Straub, et al., "Isolation, DNA sequence analysis, and mutagenesis of a proline dehydrogenase gene (putA) from *Bradyrhizobium japonicum*," *Appl. Environ. Microbiol.* 62:221 (1996).

Svab, et al., "Stable transformation of plastids in higher plants," *Proc. Natl. Acad. Sci. USA*. 87: 8526–8530 (1990).

Syntichaki, et al., "The amino–acid sequence similarity of plant glutamate dehydrogenase to the extremophilic archaeal enzyme conforms to its stress–related function," *Gene* 168: 87–92 (1996).

Szumanski & Boyle, "Analysis and sequence of the speB gene encoding agmatine ureohydrolase, a putrescine biosynthetic enzyme in *Escherichia coli*," *J. Bacteriol.* 172:538, (1990).

Teller, et al., "The glutamate dehydrogenase gene of *Clostridium symbiosum*. Cloning by polymerase chain reaction, sequence analysis and over–expression in *Escherichia coli*," *Eur. J. Biochem.* 206:151–159 (1992).

Thakur, et al., "Changes in the Electroencephalographic and γ–Aminobutyric Acid Transaminase and Succinic Semialdehyde Dehydrogenase in the Allergen Induced Rat Brain," *Biochem. Int.* 16:235–243 (1998).

Tomb, et al., "The complete genome sequence of the gastric pathogen *Helicobacter pylori*," *Nature* 388:539 (1997).

Tzimagiorgis, et al., "Molecular cloning, structure and expression analysis of a full–length mouse brain glutamate dehydrogenase cDNA," *Biochem. Biophys. Acta* 1089: 250–253 (1991).

Tzimagiorgis, et al., "Structure and expression analysis of a member of the human glutamate dehydrogenase (GLUD) gene family mapped to chromosome 10p11.2," *Hum. Genet.* 91:433–438 (1993).

Valentin et al., "Identification of 4–hydroxyhexanoic acid as a new constituent of biosynthetic polyhydroxyalkanoic acids from bacteria," *Appl. Microbiol. Biotechnol.* 40:710–16 (1994).

Valentin, et al., "Identification of 4–hydroxyvaleric acid as a constituent of biosynthetic polyhdroxyalkanoic acids from bacteria," *Appl. Microbiol. Biotechnol.* 36:507–14 (1992).

Valentin, et al., "Identification of 5-hydroxyhexanoic acid, 4-hydroxyaheptanoic acid and 4-hydroxyoctanoic acid as new constituents of bacterial polyhydroxyalkanoic acids," *Appl. Microbiol. Biotechnol.* 46:261–67 (1996).

Valentin, et al., "Production of poly(3-hydroxybutyrate-co-4-hydroxybutyrate) in recombinant *Escherichia coli* grown on glucose," *J. Biotechnol.* 58: 33–38 (1997).

Valle, et al., "Complete nucleotide sequence of the glutamate dehydrogenase gene from *Escherichia coli* K-12," *Gene* 27:193–199 (1984).

Valle, et al., "Nucleotide sequence of the promoter and amino-terminal coding region of the glutamate dehydrogenase structural gene of *Escherichia coli*," *Gene* 23: 199–209 (1983).

Wang, et al., "In vivo cloning of proline genes and its expression in *Escherichia coli*," *Chin. J. Biotechnol.* 6:27 (1990).

Watson, et al., "Isolation and Characterization of a Second Arginine Decarboxylase cDNA from Arabidopsis (Accession No. AF009647)," *Plant Physiol.* 114:1569 (1997).

Willadsen & Buckel, "Assay of 4-hydroxybutyryl-CoA dehydratase from *Clostridium aminobutyricum*," *FEMS Microbiol. Lett.* 70:187–192 (1990).

Williams, et al., "Biodegradable plastics from plants," *Chemtech* 26:38–44 (1996).

Wolff, et al., "Dehydrogenases involved in the conversion of succinate to 4-hydroxybutanoate by *Clostridium kluyveri*," *Appl. Environ. Microbiol.* 59:1876–1882 (1993).

Yee, et al., "Isolation and characterization of a NADP-dependent glutamate dehydrogenase gene from the primitive eucaryote *Giardia lamblia*," *J. Biol. Chem.* 267:7539–7544 (1992).

```
OrfZ     1  MEWEEIYKEKLVTAEKAVSKIENHSRVVFAHAVGEPVDLVNALVKNKDNYIGLEIVHMVA
            M*W   IY **
4HBCT       MDWKKIYEDRT

OrfZ    61  MGKGVYTKEGMQRHFRHNALFVGGSTRDAVNSGRAVYTPCFFYEVPSLFKEKRLPVDVAL
OrfZ   121  IQVSEPDKYGYCSFGVSNDYTKPAAESAKLVIAEVNKNMPRTLGDSFIHVSDIDYIVEAS
OrfZ   181  HPLLELQPPKLGDVEKAIGENCASLIEDGATLQLGIGAIPDAVLLFLKNKKNLGIHSEMI
OrfZ   241  SDGVMELVKAGVINNKKKTLHPGKIVVTFLMGTKKLYDFVNNNPMVETYSVDYVNNPLVI
OrfZ   301  MKNDNMVSINSCVQVDLMGQVCSESIGLKQISGVGGQVDFIRGANLSKGGKAIIAIPSTA
                                                              AIIA PS A
4HBCT                                                         AIIAMPSVA

OrfZ   361  GKGKVSRITPLLDTGAAVTTSRNEVDYVVTEYGVAHLKGKTLRNRARALINIAHPKFRES
                                  NDYVVTEYG A   K            ALINIAHP F
4HBCT                             NDADYVVTEYGIAEMK             ALINIAHPDFKDE

OrfZ   421  LMNEFKKRF
            L
4HBCT       LK
```

The sequence of the orfZ gene from C. kluyveri is:

```
ATGGAGTGGGAAGAAGATATATAAAGAGAAACTGGTAACTGCAGAAAAGCTGT
TTCAAAAATAGAAAACCATAGCAGGGTAGTTTTTGCACATGCAGTAGGAGAACC
CGTAGAGATTTAGTAAATGCACTAGTTAAAAATAAGGATAATTATATAGGACTAGA
AATAGTTCACATGGTAGCTATGGGCAAAGGTGTATATACAAAAGAGGGTATGC
AAAGACATTTTAGACATAATGCTTTTGTTTTGTAGGCGGATCTACTAGAGATGCAG
TAAATTCAGGAAGAGCAGTTTATACACCTTGTTTTTCTATGAAGTGCCAAGTTT
GTTTAAAGAAAAACGTTTGCCCTGTAGAGTAGCACTTATTCAGGTAAGTGAGCC
AGATAAATATGGCTACTGCAGTTTTGGAGTTTCCAATGACTATACCAAGCCAGC
AGCAGAAAGTGCTAAGCTTGTAATTGCAGAAGTGAATAAAAACATGCCAAGAA
CTCTTGGAGATTCTTTTATACATGTATCAGATATTGATTATATAGTGGAAGCTTC
ACACCCATTGTTAGAATTGCAGCCTCCTAAATTGGGAGATGTAGAAAAAGCCAT
AGGAGAAACTGTGCATCTTTAATTGAAGATGGAGCTACTCTTCAGCTTGGAAT
AGGTGCTATACCAGATGCGGTACTTTTATTCTTAAAGAACAAAAAGAATTTAGG
AATACATTCTGAGATGATATCAGATGGTGATGGAACTGGTGAAGGCAGGGG
TTATCAATAACAAGAAAAAGACCCTCCATCCAGGCAAAATAGTTGTAACATTTT
```

FIG. 1C

AATGGGAACAAAAAAATTATATGATTTTGTAAACAATAATCCAATGGTAGAAAC
TTATTCTGTAGATTATGTAAATAATCCACTGGTAATTATGAAAATGACAATATG
GTTTCAATAAATTCTTGTGTTCAAGTAGACTTAATGGGACAAGTATGTTCTGAAA
GTATAGGATTGAAACAGATAAGTGGAGTGGGAGGCCAGGTAGATTTTATTAGA
GGAGCTAATCTATCAAAGGGTGGAAAGGCTATTATAGCTATACCTTCCACAGCT
GGAAAAGGAAAAGTTTCAAGAATAACTCCACTTCTAGATACTGGTGCTGCAGTT
ACAACTTCTAGAAATGAAGTAGATTATGTAGTTACTGAATATGGTGTTGCTCATC
TTAAGGGCAAACTTTAAGAAAATAGGGCAAGAGCTCTAATAAATATCGCTCATC
CAAAATTCAGAGAATCATTAATGAATTTAAAAGAGATTTTAG

FIG. 1D

The sequence of the orfZ gene product is:

MEWEEIYKEKLVTAEKAVSKIENHSRVVFAHAVGEPVDLVNALVKNKDNYIGLEI
VHMVAMGKGVYTKEGMQRHFRHNALFVGGSTRDAVNSGRAVYTPCFFYEVPSL
FKEKRLPVDVALIQVSEPDKYGYCSFGVSNDYTKPAAESAKLVIAEVNKNMPRTL
GDSFIHVSDIDYIVEASHPLLELQPPKLGDVEKAIGENCASLIEDGATLQLGIGAIPD
AVLLFLKNKKNLGIHSEMISDGVMELVKAGVINNKKKTLHPGKIVVTFLMGTKK
LYDFVNNNPMVETYSVDYVNNPLVIMKNDNMVSINSCVQVDLMGQVCSESIGLK
QISGVGGQVDFIRGANLSKGGKAILAIPSTAGKGKVSRITPLLDTGAAVTTSRNEVD
YVVTEYGVAHLKGKTLRNRARALINIAHPKFRESLMNEFKKRF*

Neither the sequence of the hbcT gene from C. aminobutyricum nor the complete amino acid sequence of the corresponding enzyme is known.

FIG. 6
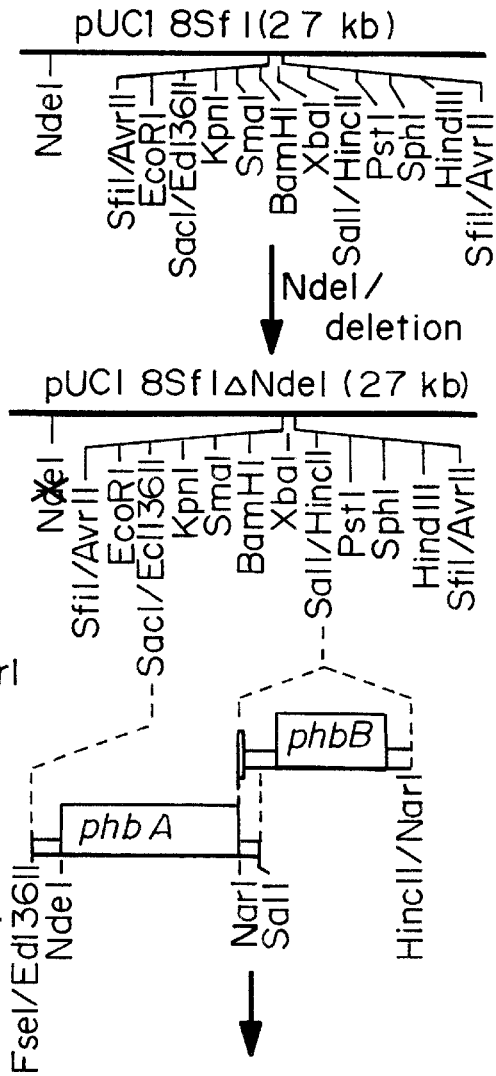
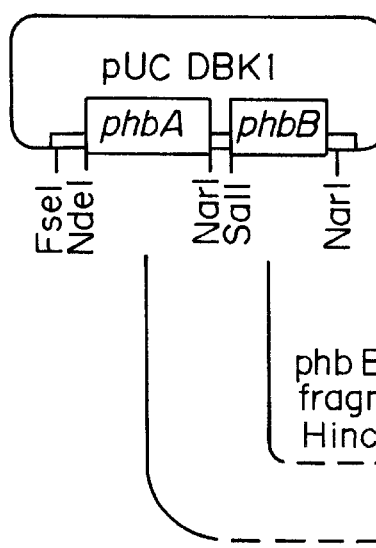
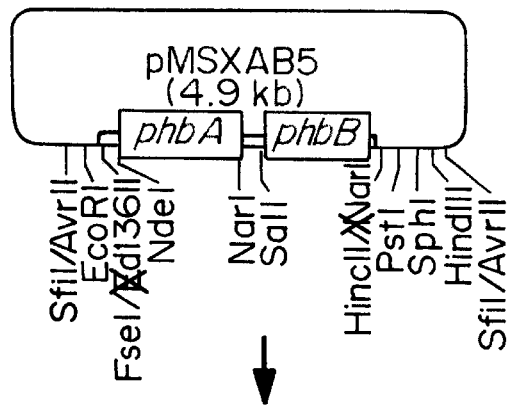
CONTINUED ON FIG. 6A

BIOLOGICAL SYSTEMS FOR MANUFACTURE OF POLYHYDROXYALKANOATE POLYMERS CONTAINING 4-HYDROXYACIDS

BACKGROUND OF THE INVENTION

This application is a continuation of U.S. Ser. No. 09/156,809 filed Sep. 18, 1998, now U.S. Pat. No. 6,316,262, which issues Nov. 13, 2001, which claims priority to U.S. Ser. No. 60/059,373 filed Sep. 19, 1997, entitled Biological Systems for the Manufacture of Polyhydroxyalkanoate Polymers containing 4-Hydroxyacids by Gjalt W. Huisman, Frank A. Skraly, David P. Martin, and Oliver P. Peoples.

Poly [(R)-3-hydroxyalkanoates] (PHAs) are biodegradable and biocompatible thermoplastic materials, produced from renewable resources, with a broad range of industrial and biomedical applications (Williams and Peoples, 1996, CHEMTECH 26, 38–44). In recent years, what was viewed as a single polymer, poly-β-hydroxybutyrate (PHB), has evolved into a broad class of polyesters with different monomer compositions and a wide range of physical properties. To date around one hundred different monomers have been incorporated into the PHA polymers (Steinbüchel and Valentin, 1995, FEMS Microbiol. Lett. 128; 219–228). It has been useful to broadly divide the PHAs into two groups according to the length of their side chains and their pathways for biosynthesis. Those with short side chains, such as polyhydroxybutyrate (PHB), a homopolymer of R-3-hydroxybutyric acid units,

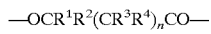

where: n is 0 or an integer and $R^1$, $R^2$, $R^3$, and $R^4$ are each selected from saturated and unsaturated hydrocarbon radicals; hal- and hydroxy-substituted radicals; hydroxy radicals; halogen radicals; nitrogen-substituted radicals; oxygen-substitued radicals; and hydrogen atoms,
are crystalline thermoplastics, whereas PHAs with long side chains are more elastomeric. The former have been known for about seventy years (Lemoigne & Roukhelman, 1925), whereas the latter materials were first identified in the early 1980's (deSmet et al., 1983, J. Bacteriol., 154; 870–878). Before this designation, however, PHAs of microbial origin containing both (R)-3-hydroxybutyric acid and one or more long side chain hydroxyacid units containing from five to sixteen carbon atoms had been identified (Steinbüchel and Wiese, 1992, Appl. Microbiol. Biotechnol. 37: 691–697; Valentin et al., 1992, Appl. Microbiol. Biotechnol. 36: 507–514; Valentin et al., 1994, Appl. Microbiol. Biotechnol. 40: 710–716; Lee et al., 1995, Appl. Microbiol. Biotechnol. 42: 901–909; Kato et al., 1996, Appl. Microbiol. Biotechnol. 45: 363–370; Abe et al., 1994, Int. J. Biol. Macromol. 16: 115–119; Valentin et al., 1996, Appl. Microbiol. Biotechnol. 46: 261–267; U.S. Pat. No. 4,876,331). A combination of the two biosynthetic pathways probably provide the hydroxyacid monomers. These latter copolymers can be referred to as PHB-co-HX. Useful examples of specific two-component copolymers include PHB-co-3-hydroxyhexanoate (Brandl et al., 1989, Int. J. Biol. Macromol. 11; 49–55; Amos and McInerey, 1991, Arch. Microbiol. 155: 103–106; Shiotani et al., 1994, U.S. Pat. No. 5,292,860). Chemical synthetic methods have also been used to prepare racemic PHB copolymers of this type for applications testing (WO 95/20614, WO 95/20615 and WO 96/20621).

Numerous microorganisms have the ability to accumulate intracellular reserves of PHA polymers. Since polyhydroxyalkanoates are natural thermoplastic polyesters, the majority of their applications are as replacements for petrochemical polymers currently in use for packaging and coating applications. The extensive range of physical properties of the PHA family of polymers, in addition to the broadening of performance obtainable by compounding and blending as traditionally performed in the polymer industry, provides a corresponding broad range of potential end-use applications. The PHAs can be produced in a wide variety of types depending on the hydroxyacid monomer composition (Steinbüchel and Valentin, 1995, FEMS Microbiol. Lett. 128: 219–228). This wide range of polymer compositions reflects an equally wide range of polymer physical properties including: a range of melting temperatures from 40° C.–180° C., glass transition temperatures from –35 to 5° C., degrees of crystallinity of 0% to 80% coupled with the ability to control the rate of crystallization and elongation to break of 5 to 500%. Poly(3-hydroxybutyrate), for example, has characteristics similar to those of polypropylene while poly(3-hydroxyoctanoate) (a copolymer of (R)-3-hydroxyoctanoate and (R)-3-hydroxyhexanoate) types behave more as elastomers and PHAs with longer side chains giving behavior closer to waxes. The PHAs can also be plasticized and blended with other polymers or agents. One particularly useful form is as a latex of PHA in water.

The monomer compositions also affect solubility in organic solvents allowing for a choice of a wide range of solvents. Copolymers of (R)-3-hydroxybutyrate and other hydroxyacid comonomers have significantly different solubility characteristics from those of the PHB homopolymer.

To date, PHAs have seen limited commercial availability with only the copolymer poly(3-hydroxybutyrate-co-3-hydroxyvalerate) (PHBV) being available in significant quantities. This copolymer has been produced by fermentation of the bacterium *Ralstonia eutropha* (formerly *Alcaligenes eutrophus*). Fermentation processes for other PHAs have been developed (Williams and Peoples, 1996, CHEMTECH 26: 38–44). Plant crops are also being genetically engineered to produce these polymers, and offer a cost structure in line with the vegetable oils and direct price competitiveness with petroleum based polymers (Williams and Peoples 1996, CHEMTECH 26: 38–44). More traditional polymer synthesis approaches have also been examined, including direct condensation and ring-opening polymerization of the corresponding lactones (Jesudason and Marchessault, 1994, Macromolecules 27: 2595–2602, U.S. Pat. Nos. 5,286,842; 5,563,239; 5,516,883; 5,461,139; Canadian patent application 2,006,508).

Synthesis of PHA polymers containing the monomer 4-hydroxybutyrate (PHB4HB, Doi, Y. 1995, Macromol. Symp. 98, 585–599) or 4-hydroxyvalerate and 4-hydroxyhexanoate containing PHA polyesters have been described (Valentin et al., 1992, Appl. Microbiol. Biotechnol. 36: 507–514 and Valentin et al., 1994, Appl. Microbiol. Biotechnol. 40: 710–716). These polyesters have been manufactured using methods similar to that originally described for PHBV in which the microorganisms are fed a relatively expensive non-carbohydrate feedstock in order to force the incorporation of the monomer into the PHA polyester. For example, production of PHB4HB has been accomplished by feeding glucose and 4-hydroxybutyrate or substrate that is converted to 4-hydroxybutyrate to *A. eutrophus* (Kunioka, M., Nakamura, Y., and Doi, Y. 1988, Polym. Commun. 29: 174; Doi, Y., Segawa, A. and Kunioka, M. 1990, Int. J. Biol. Macromo. 12: 106; Nakamura, S., Doi, Y. and Scandola, M. 1992, Macromolecules 25: 423) *A. latus* (Hiramitsu, M., Koyama, N. and Doi, Y. 1993, Biotechnol.

Lett. 15: 461), *Pseudomonas acidovorans* (Kimura, H., Yoshida, Y. and Doi, Y. 1992, Biotechnol. Lett. 14: 445) and *Comomonas acidovorans* (Saito, Y. and Doi, Y., 1994, Int. J. Biol. Macromol. 16: 18). Substrates that are converted to 4-hydroxybutyrate are 1,4-butanediol, 1,6-hexanediol, 1,8-octanediol, 1,10-decanediol, 1,12-dodecanediol and 1,4-butyrolactone. The PHB4HB copolymers can be produced with a range of monomer compositions which again provides a range of polymer properties. In particular as the amount of 4HB increases above 10 wt. %, the melting temperature ($T_m$) decreases below 130° C. and the elongation to break increases above 400% (Saito, Y., Nakamura, S., Hiramitsu, M. and Doi, Y., 1996, Polym. Int. 39: 169).

The formation of 4HB containing polymers has also been studied with recombinant strains in studies aimed at improved PHB-4HB formation in *Ralstonia eutropha* or *E. coli*. Mutants of *R. eutropha* H16 were selected that cannot use 4-hydroxybutyrate as a carbon source. When such mutants were tested for copolymer formation, up to 84% 4HB was incorporated into the accumulated PHA (Kitamura S and Y. Doi, 1994. in Biodegradable Plastics and Polyesters, 12, p. 373–378). By introducing additional copies of the phb genes, the accumulation of PHB-4HB was enhanced (Lee, Y.-H., Park, J.-S. and Huh, T.-L. 1997, Biotechnol. Lett. 19: 771–774).

It is desirable to develop more cost effective ways of producing PHAs containing 4HB by biological systems. Several factors are critical for economic production of PHA: substrate costs, fermentation time, and efficiency of downstream-processing. A general characteristic of the above described bacteria is that their growth rate is low, they are often difficult to break open and their amenity to genetic engineering is limited. Therefore, processes have been developed that improve the economics of PHA production by using transgenic organisms. Formation of PHB4HB was achieved in *E. coli* using the 4-hydroxybutyrate pathway from *C. kluyveri* (Hein, S., Söhling, B., Gottschalk, G., and Steinbüchel, A. 1997. FEMS Microbiol. Lett. 153: 411–418). In these studies both the 4-hydroxybutyryl-CoA transferase and PHA synthase were plasmid encoded. Subsequent work showed that the 4-hydroxybutyrate pathway from *C. kluyveri* supports formation of PHB-4HB in *E. coli* up to 50% of the cell dry weight from glucose as sole carbon source, and where 2.8% of the monomers is 4HB. The 4HB monomer in these strains is most likely derived from succinate, an intermediate of the TCA cycle (Valentin, H. E. and Dennis, D. 1997. J. Biotechnol. 58: 33–38). These studies were based on *Escherichia coli* as recombinant production organisms and PHA biosynthetic genes from PHA producers such as *R eutropha*.

It is an object of the present invention to provide recombinant processes whereby additional genes can be introduced in transgenic PHB producers to create new strains that synthesize monomers, such as 4HB, for alternative PHAs.

A further object of the present invention is to provide techniques and procedures to stably engineer transgenic organisms that synthesize PHAs containing 4-hydroxybutyrate either as sole constituent or as co-monomer.

It is also an object of the present invention to provide screening systems for new 4-hydroxybutyryl CoA transferase encoding genes.

It is another object of the present invention to provide techniques and procedures to engineer new pathways in biological systems for the endogenous synthesis of alternative PHA monomers.

SUMMARY OF THE INVENTION

Improved production processes for 4HB containing PHAs using transgenic strains have been developed. Transgenic *E. coli* strains are described in which the required phb genes have been integrated on the chromosome. Additional genes for the synthesis of the 4HB monomer are also integrated on the chromosome. The latter genes can be derived from a broad range of organisms which carry a 4-hydroxybutyryl-CoA transferase and be identified by screening for this activity in the engineered *E. coli* strains described here. In addition, an endogenous *E. coli* activity is disclosed that can be further improved for the purpose of 4HB-CoA transferase activity. New pathways are also disclosed for the supply of intermediates of 4HB biosynthetic pathways such as α-ketoglutarate and γ-aminobutyrate. The diversity of these pathways is important for the successful production of 4HB containing PHAs from cheap carbon sources such as sugars and fatty acids.

BRIEF DESCRIPTION OF THE DRAWINGS

FIG. 1A is the alignment of the *C. kluyveri* OrfZ sequence with the N-terminal sequence and internal sequences of 4-hydroxybutyryl CoA transferase (4HBCT) from *C. aminobutyricum* (SEQ ID Nos 1 and 2. Identical residues are indicated, similar residues are indicated by *. FIG. 1B and FIG. 1C are the nucleotide sequence of the orfZ gene from *C. kluyveri*. FIG. 1D is the amino acid sequence of the orfZ gene from *C. kluyveri*.

FIG. 6 and FIG. 6A a schematic of the construction of plasmids for integration of 3-ketoacyl-CoA thiolase (phbA) and acetoacetyl-CoA reductase (phbB) genes from *Z. ramigera* into the chromosome of *E. coli* and other Gram-negative bacteria.

DETAILED DESCRIPTION OF THE INVENTION

Figure 2:
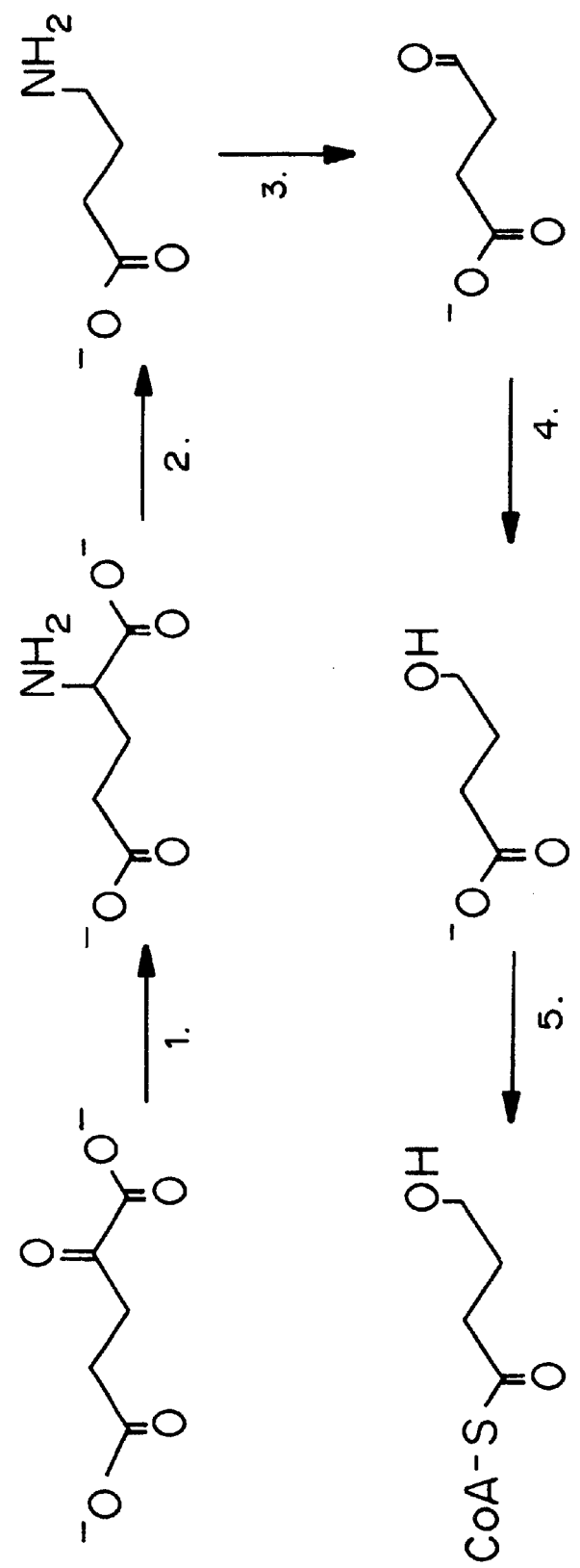
FIG. 2 is a schematic of the endogenous synthesis of 4-hydroxybutyryl CoA from α-ketoglutarate through the GABA shunt. 1. α-ketoglutarate aminotransferase; 2. glutamate decarboxylase; 3. GABA transaminase; 4. Succinic semialdehyde reductase; 5. 4-hydroxybutyryl CoA transferase.

The minimal biological requirement for the synthesis of poly(3-hydroxybutyrate-co-4-hydroxybutyrate) have been defined. Enzymatic synthesis of the substrates for PHA synthase from R. eutropha was achieved by incubation of equimolar amounts of (R)-3-hydroxybutyrate with 4-hydroxybutyrate CoA transferase. In situ monomer-CoA synthesis coupled by direct enzymatic polymerization results in the formation of a PHB-4HB copolymer as determined by $^1$H-NMR of the resulting polymer. Techniques and procedures to engineer transgenic organisms that synthesize PHAs containing 4-hydroxybutyrate either as sole constituent or as co-monomer have been developed. In these systems the transgenic organism is either a bacterium eg. Escherichia coli, K. pneumoniae, Ralstonia eutropha (formerly Alcaligenes eutrophus), Alcaligenes latus or other microorganisms able to synthesize PHAs, or a higher plant or plant component, such as the seed of an oil crop (Brassica, sunflower, soybean, corn, safflower, flax, palm or coconut or starch accumulating plants (potato, tapioca, cassava). A screening procedure for the identification of genes encoding enzymes capable of converting 4-hydroxybutyric acid to 4-hydroxybutyryl-CoA and methods for redirecting the flux of normal cellular metabolites such as e.g. succinic acid and/or glutamic acid to 4-hydroxybutyric acid has been developed. The gene encoding a 4-hydroxybutyryl CoA transferase gene from the Gram-positive, strict anaerobic bacterium Clostridium kluyveri has been identified and used to express this enzyme activity in a transgenic organism to convert 4-hydroxybutyric acid into 4-hydroxybutyryl-CoA resulting in the accumulation of poly(4-hydroxybutyrate) in E. coli. A bacteria expressing a functional PHA synthase from a transgene is described, as well as methods for expressing these genes in transgenic plant crops.

Screening systems for new 4-hydroxybutyryl CoA transferase encoding genes are also described. Transgenic E. coli strains in which a PHA synthase encoding gene is integrated in the chromosome and expressed to levels supporting PHA synthesis have been developed. With these transgenic strains can be screened with genomic libraries from different biological sources for activities that convert alternative PHA precursors such as 4-hydroxybutyrate to corresponding substrates for PHA synthase.

Techniques and procedures are provided to engineer new pathways in biological systems for the endogenous synthesis of alternative PHA monomers. Metabolism of any PHA production organism, including bacteria and plant crops, can be redirected to supply specific metabolites for PHA synthesis by metabolic engineering. In order to make this approach effective, it is necessary to develop new biochemical pathways leading to the desired monomer from one of the common metabolic intermediates. It is not necessary that such pathways exist in one organism since the individual steps can be reconstituted in the production organism of choice using genetic engineering techniques.

Incorporation of alternative monomers derived from supplemented feedstocks has specific drawbacks. First, additional feeds into a fermenter are costly as they expand the infrastructure and impose additional quality control. Second, addition of monomer precursors needs to be tightly controlled to achieve a constant composition of the monomer pools and PHA composition. Methods to engineer E. coli such at P(4HB) or PHB-co-4HB synthesis occurs from inexpensive carbohydrate feedstocks such as glucose, sucrose, xylose and lactose as the only carbon source. Enzyme activities in the γ-hydroxybutyrate shunt are elevated, while enzyme activities that drain intermediates from this shunt are reduced. An alternative pathway yields 4HB from succinate. A similar approach in metabolic engineering can accommodate production of 4HB containing PHAs in organisms such as A. eutrophus, A. latus and Comamonas which are currently capable of producing 4-hydroxybutyrate copolymers from cosubstrates and in transgenic microbial and plant crop systems expressing a PHA synthesis from a heterologous PHA synthase gene or genes.

It is crucial for efficient PHA synthesis in recombinant E. coli strains that the expression of all the genes involved in the pathway be adequate. To this end, the genes of interest can be expressed from extrachromosomal DNA molecules such as plasmids, which intrinsically results in a copy number effect and consequently high expression levels, or, more preferably, they can be expressed from the chromosome. For large scale fermentations of commodity type products it is generally known that plasmid-based systems are unsatisfactory due to the extra burden of maintaining the plasmids and the problems of stable expression. These drawbacks can be overcome using chromosomally encoded enzymes by improving the transcriptional and translational signals preceding the gene of interest such that expression is sufficient and stable.

Production of 4HB Copolymers

Gerngross and Martin reported that substrates of PHA synthase require the presence of a coenzyme A (CoA) moiety (Gerngross, T. U. and Martin, D. P. (1955) Proc. Natl. Acad. Sci. USA 92:6279). The precursor required for the incorporation of 4HB is therefore 4HB-CoA. To determine the minimal requirement for the synthesis of 4-hydroxybutyrate containing PHAs, a mixture of 4-hydroxybutyrate, 3-hydroxybutyrate, 4-hydroxybutyrate CoA transferase purified from Clostridium acetobutylicum (Willadsen and Buckel, FEMS Microbiol. Lett. (1990) 70: 187–192) and PHB synthase (as purified by Gerngross et al. (1994) Biochemistry 33: 9311) was incubated in vitro under conditions as described by Gerngross and Martin (Gerngross, T. U. and Martin, D. P. (1995) Proc. Natl. Acad. Sci. USA 92:6279. The product of the reaction was isolated and the incorporation of 4-hydroxybutyrate was confirmed by 1H-NMR.

Having established the minimal requirements for the synthesis of 4-hydroxybutyrate containing PHA in vitro, it becomes evident that the minimal requirements for the synthesis of these PHAs in vivo includes a gene encoding 4-hydroxybutyrate CoA transferase or similar activity and 4-hydroxybutyrate. The substrate 4-hydroxybutyrate can be administered to the PHA producing microorganism or be synthesized in vivo by engineered biosynthetic pathways from appropriate substrates. Amino acid sequence was determined for the purified 4-hydroxybutyrate CoA transferase (Scherf and Buckel, Appl. Environ. Microbiol. (1991) 57:2699–2701). The purified protein was subjected to enzymatic digestion followed by amino acid sequence analysis of three of the resulting peptides. The amino acid sequence of these peptides and the N-terminus of the intact protein showed a striking homology to the OrfZ gene product (FIGS. 1A, 1B, and 1C), whose identity and function was not known, thereby identifying orfZ as the gene encoding 4-hydroxybutyryl CoA transferase in *C. kluyveri*. This gene was renamed hbcT.

Confirmation that introduction of this gene into an *E. coli* strain that expresses PHB synthase is sufficient for 4-hydroxybutyrate containing PHA synthesis was obtained as follows. The PHB synthase from *Z. ramigera* is expressed from a chromosomally integrated copy of this gene in *E. coli* strain MBX379. PHA was formed within the cells upon introduction of a plasmid encoding hbcT and supplying 4-hydroxybutyrate in the growth medium. In the absence of genes providing other enzymes of the PHB pathway, the accumulated PHA is P4HB. *E. coli* strain MBX777 contains the genes encoding β-ketothiolase, acetoacetyl CoA reductase and PHB synthase from *Z. ramigera*. Upon introduction of a plasmid encoding hbcT and supplying 4-hydroxybutyrate in the growth medium, a PHB-4HB copolymer was formed.

Further development of a PHB-4HB producing system is achieved by engineering the metabolic pathways of the transgenic organism such that 4-hydroxybutyrate is synthesized from endogenous intermediates instead of being supplied externally. Two biochemical routes to the precursor 4HB-CoA can be established in a production organism for 4HB-containing PHAs. The first pathway proceeds from α-ketoglutarate, the second from succinate. Substrate for both pathways can also be provided through amino acid degradation.

Pathway to 4-Hydroxybutyryl CoA from α-Ketoglutarate

A pathway that enables the conversion of α-ketoglutarate to 4-hydroxybutyryl CoA is shown in FIG. 2. Enzymes involved in this pathway are α-ketoglutarate transaminase, glutamate dehydrogenase, glutamate decarboxylase, 4-hydroxybutyrate dehydrogenase and 4-hydroxybutyrate CoA transferase.

Genes encoding these activities can be acquired from multiple sources:

gdhA gene encoding glutamate dehydrogenase: *E. coli* (Valle et al. Gene (1984) 27: 193–199 and Valle et al., Gene (1983) 23: 199–209), *Klebsiella aerogenes* (Mountain et al., Mol. Gen. Genet. (1985) 199:141–145), *Pyrococcus furiosus* (DiRuggiero et al., Appl. Environ. Microbiol. (1995) 61: 159–164; Eggen et al., Gene (1993) 132:143–148), *Sulfolobus shibatae* (Benachenhou et al. (1994), Gene 140: 17–24), *Rumonococcus flavefaciens* (Duncan et al., Appl, Environ. Microbiol. (1992) 58: 4032–4037), *Pseudomonas fluorescens* (Miyamoto et al., J. Biochem. (1992) 112:52–56), *Clostridium symbiosum* (Teller et al., Eur. J. Biochem. (1992) 206: 151–159), *Synechocystis* (Plant Mol. Biol. (1995) 28: 173–188), *Corynebacterium glutamicum* (Bormann et al., Mol. Microbiol. (1992) 6:301–308), *Peptostreptococcus asaccharolyticus* (Snedecor et al. (1991) J. Bacteriol. 173: 6162–6167), *Salmonella typhimurium* (Miller et al. (1984) J. Bacteriol. 157: 171–178), *Chlorella sorokiniana* (Cock et al., Plant Mol. Biol. (1991) 17: 1023–144), *Saccharomyces cerevisiae* (Nagasu et al., Gene (1984) 37:247–253), *Neurospora crassa* (Kinnaird et al., Gene (1983) 26:253–260), *Giardia lamblia* (Yee et al (1992) J. Biol. Chem. 267: 7539–7544).

gadA and/or gadB encoding glutamate-succinic semialdehyde transaminase: *E. coli* (Metzer and Halpern, J. Bacteriol. (1990) 172: 3250–3256 and Bartsch et al. J. Bacteriol. (1990) 172: 7035–7042) or *S. cerevisiae* (André and Jauniaux, Nucl. Acid Res. (1990) 18: 3049).

4hbD gene encoding the 4-hydroxybutyrate dehydrogenase: *C. kluyveri* (Söhling and Gottschalk, 1996, J. Bacteriol. 178, 871–880).

4-hydroxybutyryl CoA transferase gene: *C. aminobutyricum* (Willadsen and Buckel, FEMS Microbiol. Lett. (1990) 70: 187–192) or: *C. kluyveri* (Söhling and Gottschalk, 1996, J. Bacteriol. 178, 871–880).

Other sources of these genes in addition to the listed microorganisms which are of mammalian or plant origin:

Glutamate dehydrogenase: (Syntichaki et al. (1996) Gene 168: 87–92), maize (Sakakibara et al. (1995), Plant Cell Physiol. 36: 789–797), human (Tzimagiogis et al. (1993), Hum. Genet. 91: 433–438), mouse (Tzimagiogis et al. (1991), Biochem. Biophys. Acta 1089: 250–253), Amuro et al. (1990), Biochem. Biophys. Acta 1049: 216–218).

α-ketoglutarate transaminase: (Park et al. (1993), J. Biol. Chem. 268: 7636–7639), Kwon et al. (1992), J. Biol. Chem. 267: 7215–7216), rat (Thakur et al. (1988), Biochem. Int. 16:235–243), rabbit (Kirby et al. (1985), Biochem. J. 230: 481–488).

glutamate decarboxylase: tomato (Gallego et al. (1995), Plant Mol. Biol. 27: 1143–1151), human (Bu et al. (1994), Genomics 21:222–228), cat (Chu et al. (1994), Arch. Biochem. Biophys. 313: 287–295), plant (Baum et al. (1993), J. Biol. Chem. 268: 19610–19617).

Regulation of glutamate dehydrogenase expression has been studied primarily in *E. coli*. The corresponding gdhA gene is highly expressed in glucose/ammonia minimal medium and moderately catabolite repressed. Excess glutamate is degraded by aspartate aminotransferase (encoded by aspC). Two REP sequences downstream of the glutamate dehydrogenase gene are involved in mRNA stabilization. The *P. fluorescens* glutamate dehydrogenase gene shows similar regulation by glucose. Glutamate dehydrogenase from both *P. furiosus* and *C. glutamicum* is expressed in *E. coli* because they complement a gdhA mutation.

The gab gene cluster is only expressed at low constitutive levels due to catabolite repression by glucose and ammonia. When a poor nitrogen source or succinate as carbon source are supplied the operon is derepressed. Thus, both cAMP/CRP and NtrC regulate the promoter, in addition to a specific repressor encoded by gabC. The promoter that regulates gabT is located upstream of gabD. Succinate semialdehyde dehydrogenases are encoded by gabD and sad. These activities could be deleterious for the purpose of P4HB or PHB-4HB production although their expression is expected to be repressed by the presence of sufficient glucose and nitrogen sources. Glutamate decarboxylase is a rare enzyme among the Enterobacteriacea. It is pyridoxal phosphate dependent and well expressed at low pH.

Figure 3:
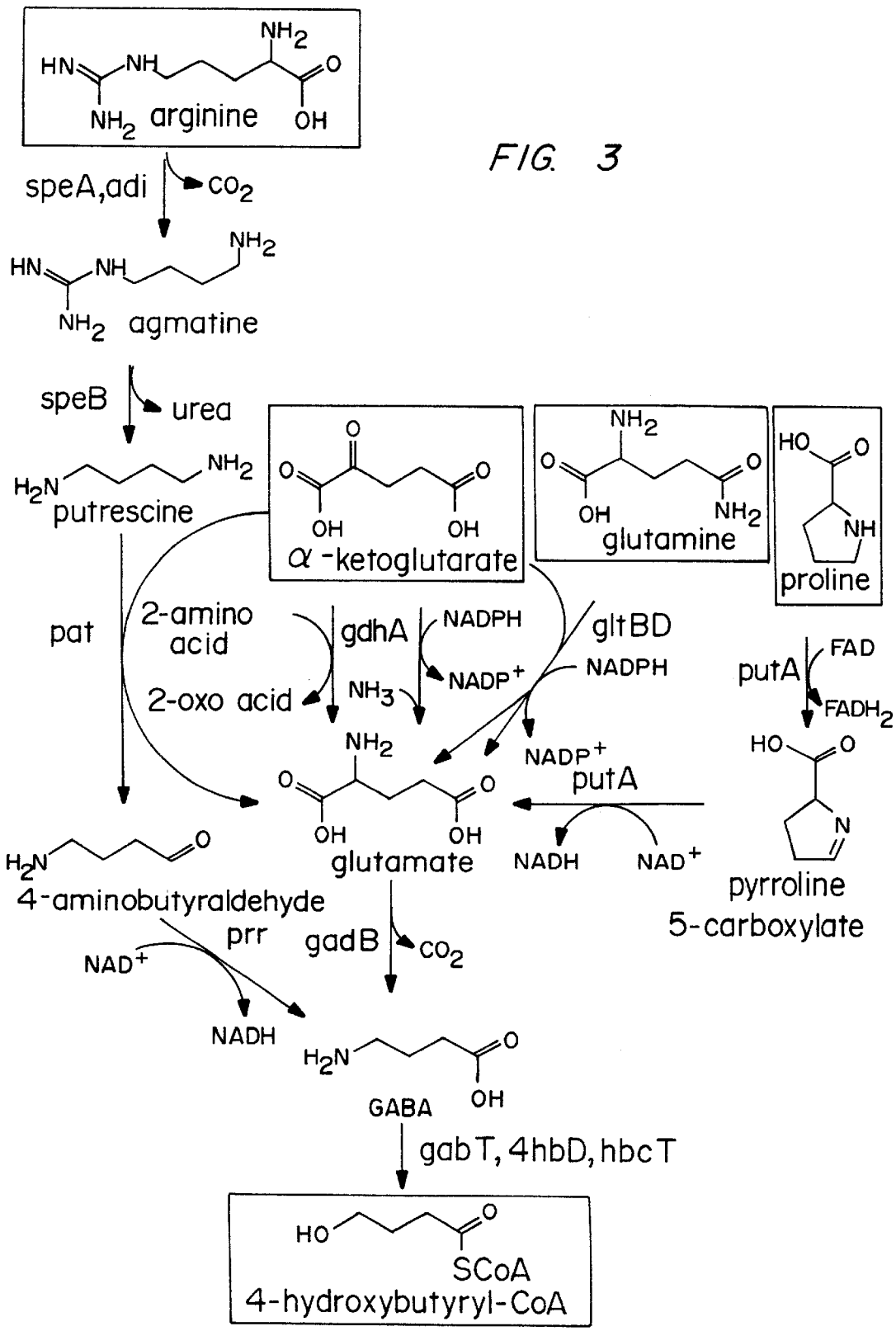
FIG. 3 is a schematic of the endogenous synthesis of 4-hydroxybutyryl-CoA from GABA precursors. GABA is an intermediate in the degradation of amino acids such as arginine, glutamine and proline. Genes in arginine degradation are encoded by speA, adi, speB, pat and prr; genes in glutamine degradation are encoded by gltBD and gadB, genes in proline degradation are encoded by putA and gadB. GABA is converted to 4-hydroxybutyryl-CoA by the gene products of gabT, 4hbD and hbcT.

Pathways to 4-hydroxybutyryl-CoA from arginine, putrescine, glutamine and proline via GABA Bacteria such as *Escherichia coli* are capable of catabolizing at least four different amino acids (arginine, proline, glutamine, and glutamate) to produce GABA, which can be converted as described above to 4-hydroxy-butyryl-CoA. These catabolic pathways are depicted in FIG. 3.

*E. coli* contains at least two activities, encoded by speA and adi, that can decarboxylate arginine to agmatine. Putrescine and urea are formed from agmatine by the action of agmatine ureohydrolase, encoded by speB. Putrescine donates an amino group to α-ketoglutarate to form 4-aminobutyraldehyde and glutamate in a reaction catalyzed by the product of the pat gene, putrescine aminotransferase. The 4-aminobutyraldehyde is oxidized to GABA by aminobutyraldehyde dehydrogenase, encoded by prr. The synthesis of agmatine ureohydrolase, putrescine aminotransferase, and aminobutyraldehyde dehydrogenase is dually controlled by catabolite repression and nitrogen availability. Catabolite repression of agmatine ureohydrolase, but not that of putrescine aminotransferase or aminobutyraldehyde dehydrogenase, can be relieved by cAMP. Agmatine ureohydrolase synthesis is induced by arginine and agmatine. Arginine decarboxylase synthesis is not sensitive to catabolite repression or to stimulation by nitrogen limitation or subject to substrate induction (Shaibe et al., J. Bacteriol. 163:938, 1995). There is a second arginine decarboxylase in *E. coli* which appears to be specialized for catabolism rather than biosynthesis of arginine, and this protein is encoded by the adi gene (Stim and Bennett, J. Bacteriol. 175:1221, 1993). It is induced under conditions of acidic pH, anaerobiosis, and rich medium.

Proline is degraded in *E. coli* by the product of the putA gene, which catalyzes successive oxidations of proline to pyrroline 5-carboxylate and then to glutamate. The first step is FAD-dependent, and thus the PutA protein is membrane-associated. This same protein also acts as a repressor of the put operon in the absence of proline. The put operon is subject to catabolite repression (McFall and Newman, pp. 358–379, in Neidhardt, ed., *Escherichia coli* and *Salmonella typhimurium*: cellular and molecular biology, ASM Press, Washington, D.C., 1996).

Glutamine is converted to glutamate in *E. coli* by glutamate synthase, the product of the gltB and gltD genes. Two molecules of glutamate are formed by the donation of an amino group by glutamine to α-ketoglutarate. The activity of *E. coli* glutamate synthase is high when this organism is grown in ammonia-containing minimal medium and low when it is grown in the presence of glutamate or glutamate-generating nitrogen sources if nitrogen is limiting (Reitzer, pp. 391–407, in Neidhardt, ed., *Escherichia coli* and *Salmonella typhimurium*: cellular and molecular biology, ASM Press, Washington, D.C., 1996).

These pathways can be realized for the production of poly(4-hydroxybutyrate) in an organism such as *E. coli* by relying upon the organism's own genes or by importing such genes from another source into the organism of interest. These genes can be acquired from many organisms, such as:

speA encoding arginine decarboxylase: *Escherichia coli* (Moore and Boyle, J. Bacteriol. 172:4631, 1990), Synechocystis sp. (Kaneko et al., DNA Res. 3:109, 1996), *Helicobacter pylori* (Tomb et al., Nature 388:539, 1997), thale cress (*Arabidopsis thaliana*) (Watson et al., Plant Physiol. 114:1569, 1997), soybean (*Glycine max*) (Nam et al., Plant Cell Physiol. 38:1156, 1997), clove pink (*Dianthus caryophyllus*) (Chang et al., Plant Physiol. 112:863, 1996), pea (*Pisum sativum*) (Perez-Amador et al., Plant Mol. Biol. 28:997, 1995), tomato (*Lycopersicon esculentum*) (Rastogi et al., Plant Physiol. 103:829, 1993), oat (*Avena sativa*) (Bell and Malmberg, Mol. Gen. Genet. 224:431, 1990), plants of the family Brassicaceae (*Barbarea vulgaris, Nasturtium officinale, Arabis drummondii, Aethionema grandiflora, Capsella bursa-pastoris, Arabidopsis arenosa, Sisymbrium altissimum, Thellungiella salsuginea, Polanisia dodecandra, Stanleya pinnata, Carica papaya, Brassica oleracea, Brassica nigra, Theobroma cacao*) (Galloway et al., Mol. Biol. Evol. 15, 1998), rat (Morrissey et al., Kidney Int. 47:1458, 1995).

adi encoding biodegradative arginine decarboxylase: *Escherichia coil* (Stim and Bennett, J. Bacteriol. 175:1221, 1993).

speB encoding agmatine ureohydrolase: *Escherichia coli* (Szumanski and Boyle, J. Bacteriol. 172:538, 1990), *Streptomyces clavuligerus* (Aidoo et al., Gene 147:41, 1994), *Bacillus subtilis* (Presecan et al., Microbiology 143:3313, 1997), Synechocystis sp. (Kaneko et al., DNA Res. 3:109, 1996), *Methanobacterium thermoautotrophicum* (Smith et al., J. Bacteriol. 179:7135, 1997), *Archaeoglobus fulgidus* (Klenk et al., Nature 390:364, 1997).

pat encoding putrescine aminotransferase and prr encoding aminobutyraldehyde dehydrogenase: *Escherichia coli* (Shaibe et al., J. Bacteriol. 163:938, 1985).

gltBD encoding glutamate synthase: *Escherichia coli* (Oliver et al., Gene 60:1, 1987), *Aquifex aeolicus* (Deckert et al., Nature 392:353, 1998), *Azospirillum brasilense* (Pelanda et al., J. Biol. Chem. 268:3099, 1993), alfalfa (*Medicago sativa*) (Gregerson et al., Plant Cell 5:215, 1993), baker's yeast (*Saccharomyces cerevisiae*) (Filetici et al., Yeast 12:1359, 1996; Cogoni et al., J. Bacteriol. 177:792, 1995), *Methanococcus jannaschii* (Bult et al., Science 273:1058, 1996), *Methanobacterium thermoautotrophicum* (Smith et al., J. Bacteriol. 179:7135, 1997), *Bacillus subtilis* (Petit et al., Mol. Microbiol. 29:261, 1998), *Azospirillum brasilense* (Mandal and Ghosh, J. Bacteriol. 175:8024, 1993).

putA encoding pyrroline-5-carboxylate reductase: *Streptomyces coelicolor* (Redenbach et al., Mol. Microbiol. 21:77, 1996), *Mycobacterium tuberculosis* (Cole et al., Nature 393:537, 1998), *Haemophilus influenzae* (Fleischmann et al., Science 269:496, 1995), *Escherichia coli* (Blattner et al., Science 277:1453, 1997), baker's yeast (*Saccharomyces cerevisiae*) (Science 265:2077, 1994), *Vibrio alginolyticus* (Nakamura et al., Biochim. Biophys. Acta 1277:201, 1996), *Pseudomonas aeruginosa* (Savoiz et al., Gene 86:107, 1990), *Klebsiella pneumoniae* (Chen and Maloy, J. Bacteriol. 173:783, 1991), *Salmonella typhimurium* (Allen et al., Nucleic Acids Res. 21:1676, 1993), *Agrobacterium tumefaciens* (Cho et al., J. Bacteriol. 178:1872, 1996), *Sinorhizobium meliloti* (Jimenez-Zurdo et al., Mol. Microbiol. 23:85, 1997), *Rhodobacter capsulatus* (Keuntje et al., J. Bacteriol. 177:6432, 1995), *Bradyrhizobium japonicum* (Straub et al., Appl. Environ. Microbiol. 62:221, 1996), Synechocystis sp. (Kaneko et al., DNA Res. 3:109, 1996), Shewanella sp. (Kato et al., J. Biochem. 120:301, 1996), *Photobacterium leiognathi* (Lin et al., Biochem. Biophys. Res. Commun. 219:868, 1996), *Helicobacter pylori* (Tomb et al., Nature 388:539, 1997), cultivated mushroom (*Agaricus bisporus*) (Schaap et al., Appl. Environ. Microbiol. 63:57, 1997), soybean (*Glycine max*) (Delauney and Verma, Mol. Gen. Genet. 221:299, 1990), human (*Homo sapiens*) (Campbell et al., Hum. Genet. 101:69, 1997).

The arginine, proline, glutamine, or glutamate can be supplied exogenously to the poly(4-hydroxybutyrate)-producing organism, or it can be synthesized in the host from another carbon source, preferably an inexpensive one such as glucose. *E. coli*, for example, synthesizes all of these compounds from glucose, but generally only to an extent sufficient for growth.

Strains of *E. coli* that overproduce these compounds have been developed. Tujimoto et al. (U.S. Pat. No. 5,378,616) describe an *E. coli* mutant that accumulates glutamate. Momose et al. (U.S. Pat. No. 4,430,430) describe the overexpression of the argA gene in *E. coli*, which leads to arginine accumulation. Proline-resistant mutants of *E. coli* that overexpress proline synthesis genes can accumulate proline (Wang et al., Chin. J. Biotechnol. 6:27, 1990). Tobacco plants which overexpress bacterial proline synthesis genes were also shown to accumulate proline (Sokhansandzh et al., Genetika 33:906, 1997). Furthermore, E. coli and other bacteria accumulate glutamate, GABA, and proline as a response to high medium osmolarity (McLaggan et al., J. Biol. Chem. 269:1911, 1994; Measures, J. C., Nature 257:398, 1975; Schleyer et al., Arch. Microbiol. 160:424, 1993; Botsford et al., Appl. Environ. Microbiol. 60:2568, 1994).

Pathway to 4-Hydroxybutyryl CoA from Succinate

The complete biochemical pathway for the conversion of succinate to 4HB-CoA (FIG. 4) has been characterized in *Clostridium kluyveri* (Söhling and Gottschalk, 1993, Eur. J. Biochem. 212, 121–127; Wolff et al., 1993, Appl. Environ. Microbiol. 59, 1876–1882; Scherf et al., 1994, Arch. Microbiol. 161, 239–245). More recently, the genes encoding the *C. kluyveri* succinyl-CoA: CoA transferase (catI), succinate-semialdehyde dehydrogenase (sucD) and 4-hydroxybutyrate dehydrogenase (4hbD) have been identified (Söhling and Gottschalk, 1996, J. Bacteriol. 178, 871–880). These genes are located in a contiguous stretch of DNA on the *C. kluyveri* chromosome and flanked by three genes of unknown function (orfZ, orfY and sigL). The genes appear to be induced by succinate in the growth medium. The gene encoding 4-hydroxybutyryl CoA transferase was not identified in these studies.

Identification of Alternative Genes Encoding Enzymes that Operate in the Synthesis of 4-Hydroxybutyrate Alternative genes encoding enzymes that operate in the conversion of either α-ketoglutarate or succinate to 4HB can be isolated by complementation or expression studies: glutamate-succinic semialdehyde transaminase genes can be isolated from gene libraries because of the ability of this gene to complement an *E. coli* gabT mutation for utilization of γ-aminobutyric acid as nitrogen source. Likewise, mutations in glutamate dehydrogenase and glutamate decarboxylase genes in *E. coli* can be complemented. Expression of alternative 4-hydroxybutyrate dehydrogenase genes will allow *E. coli* to utilize 4-hydroxybutyrate as a carbon source. Enzyme homology searches using the BLASTP program and the GenBank database suggest the presence of 4-hydroxybutyrate dehydrogenase homologs in the *E. coli* genome. These proteins have been identified with the genetic index numbers: gi|1788795and gi|1790015.

Importance of Integration, Screening for Polymer Production

It is important for efficient PHA production that strains do not lose the capability to synthesize the biopolymer for the duration of the inoculum train and the production run. Loss of any of the phb genes results in loss of product whereas loss of any of the genes that provide new monomers results in heterogeneous product formation. Both are undesirable and stable propagation of the strain is therefore required. Unfortunately, merely integrating the gene encoding the transferase or synthase does not result in significant polymer production. It is necessary to enhance enzyme expression, through alteration of the promoter region or mutagenesis or other known techniques, followed by screening for polymer production. Using these techniques, integration of the genes in the strains described in the examples was determined to be stable for at least 50 generations, sufficient for production in 100,000 L vessels.

Growth and morphology of these recombinant PHA producers is not compromised by the presence of phb genes on the chromosome. During the selection procedures, individual integrants are selected on minimal medium plates circumventing the isolation of auxotrophic strains. Growth rates of the different phb integrants were similar to that of the wild-type *E. coli* strains from which the PHB producers were derived. The addition of the phb genes to the *E. coli* chromosome did not affect the downstream processing of these strains, as they were still easily lysed by conventional methods.

The present invention will be further understood by reference to the following non-limiting examples.

Example 1
Minimal Requirements for PHB-4HB Synthesis

It has been previously shown that the minimum requirements for the synthesis of poly-(R-3-hydroxybutyrate) (PHB) are the purified PHA synthase from *A. eutrophus* and the substrate (R)-3-hydroxybutyryl-CoA. 4-Hydroxybutyryl-CoA can be prepared in situ from acetyl-CoA and 4-hydroxybutyrate via a transthioesterification reaction catalyzed by the enzyme 4-hydroxybutyryl-CoA transferase, isolated from *Clostridium aminobutyricum*. This enzyme will also catalyze the formation of (R)-3-hydroxybutyryl-CoA from the free acid and acetyl-CoA. Thus the minimum requirements for the in situ synthesis of 4-hydroxybutyryl-CoA and its co-polymerization with (R)-3-hydroxybutyryl-CoA to form P(3HB-co-4HB) would include PHA synthase, (R)-3-hydroxybutyric acid, 4-hydroxybutyric acid, acetyl-CoA and 4-hydroxybutyryl-CoA transferase in a buffered aqueous solution. This was demonstrated as follows:

To potassium phosphate buffer (1 ml, 100 mM, pH 7.5) the following were added:
acetyl-CoA (0.5 mL, 30 mM)
4-hydoxybutyric acid sodium salt (50 µl, 2 M)
(R)-3-hydroxybutyric acid sodium salt (100 µl, 1 M)
4-hydroxybutyryl-CoA transferase (10 mg, 25 units)
PHA synthase (0.05 mg)

The reaction was allowed to stand at room temperature overnight. The formation of insoluble PHA granules was noted. Insoluble material was pelleted by centrifugation and freeze dried (0.65 mg). This material had a sticky consistency. Organic material was extracted with $CDCl_3$ and analyzed by $^1$H-NMR. NMR analysis confirmed the formation of poly-((R)-3-hydroxybutyrate-co-4-hydroxybutyrate) containing approximately 20% 4-hydroxybutyric acid. The NMR spectrum matches a literature spectrum of poly-((R)-3-hydroxybutyrate-co-4-hydroxybutyrate) (Doi, Y. et al., Macromolecules 1988, 21: 2722–2727).

Example 2
Poly(4-Hydroxybutyrate) (P4HB) Synthesis in *E. coli* Using a Plasmid Encoded Pathway The hbcT gene from *C. kluyveri* was expressed in *E. coli* using standard molecular biological techniques. The gene is placed in an appropriate vector behind a strong promoter and under conditions that drive expression from this promoter. 4HBCT is produced.

Strains of *E. coli* were equipped with plasmid pFS30 which contains the genes encoding 4-hydroxybutyryl-CoA transferase from *C. kluyveri* and PHB synthase from *R. eutropha*. These genes are expected to convert 4-hydroxybutyric acid into 4-hydroxybutyryl-CoA which is subsequently polymerized to poly(4-hydroxybutyrate). Strains were grown in 250 ml Erlenmeyer flasks containing 50 to 100 ml 10% LB liquid medium with 4-hydroxybutyrate, alone or in combination with glucose, as carbon source. Cultures were incubated at 30 to 33° C. with shaking at 150 or 200 rpm. Cultures were harvested after 24 hours of incubation and analyzed for PHA. *E. coli* MBX1177 (a spontaneous mutant of strain DH5α selected for growth on minimal 4-HB medium) with pFS30 accumulates 67% of its cell dry weight as a P4HB homopolymer:

| host | volume | rpm | 4HB | glc | T | % LB | % PHA | F (4HB) |
|---|---|---|---|---|---|---|---|---|
| 19 | 50 ml | 150 | 5 | 2 | 33 | 10 | <5 | 1.0 |
| 184 | 100 ml | 150 | 5 | 2 | 33 | 10 | 38.9 | 1.0 |
| 816 | 100 ml | 200 | 5 | 0 | 32 | 10 | 19.3 | >0.99 |
| 817 | 100 ml | 200 | 5 | 0 | 32 | 10 | 12.8 | >0.99 |
| 821 | 100 ml | 200 | 5 | 0 | 32 | 10 | 24.8 | >0.99 |
| 1177 | 50 ml | 150 | 5 | 0 | 33 | 10 | 14.8 | 1.0 |
| 1177 | 100 ml | 200 | 5 | 2 | 30 | 10 | 67.1 | 1.0 |

Example 3
Poly(4-Hydroxybutyrate) (P4HB) Synthesis in *E. coli* Using a Plasmid Encoded PHA Synthase Strains of *E. coli* were equipped with plasmid pFS16, which contains the gene encoding 4-hydroxybutyryl-CoA transferase from *C. kluyveri*. This gene is expected to convert 4-hydroxybutyric acid into 4-hydroxybutyryl-CoA which is subsequently polymerized by a chromosomally encoded PHB synthase into P4HB. Strains were grown in 250 ml Erlenmeyer flasks containing 50 to 100 ml 10% LB or 100% LB liquid medium with 4-hydroxybutyrate, alone or in combination with glucose, as carbon source. Cultures were incubated at 32 to 37° C. with shaking at 0 to 250 rpm. Cultures were harvested after 24 hours of incubation and analyzed for PHA. *E. coli* MBX769 with pFS 16 accumulates 67% of its cell dry weight as a P4HB homopolymer. Formation of 4HB containing PHAs is consequently not dependent on a plasmid encoded PHB synthase.

| host | volume | rpm | 4HB | glc | T | % LB | % PHA | F (4HB) |
|---|---|---|---|---|---|---|---|---|
| 777 | 50 ml | 250 | 5 | 0 | 37 | 100 | 7.6 | 0.36 |
| 769 | 50 ml | 250 | 5 | 0 | 37 | 100 | 0 | — |
| 769 | 50 ml | 100 | 5 | 0 | 33 | 10 | 8.0 | 0.18 |
| 769 | 100 ml | 150 | 5 | 2 | 33 | 10 | 16.4 | 0.25 |
| 769 | 100 ml | 200 | 5 | 2 | 32 | 10 | 43.5 | 0.37 |
| 769 | 100 ml | 0 | 5 | 0 | 33 | 10 | 13.6 | 0.29 |
| 769 | 100 ml | 0 | 5 | 0 | 33 | 10 | 19.8 | 0.32 |
| 769 | 100 ml | 250 | 5 | 0 | 37 | 10 | 2.4 | 0.002 |

Example 4
Construction of Plasmids for Chromosomal Integration of phb Genes.

Figure 5:
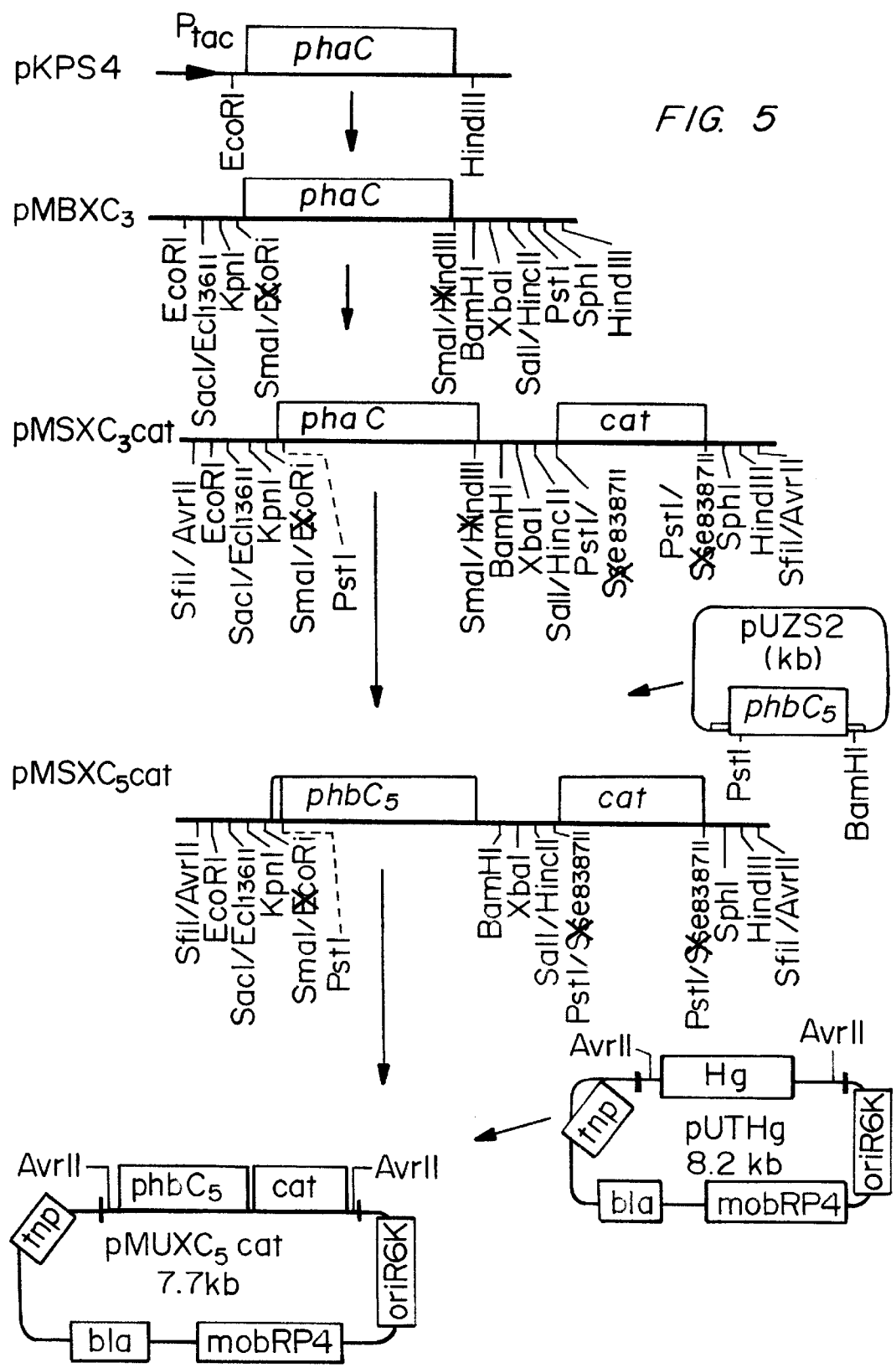
FIG. 5 is a schematic of the construction of plasmids for integration of the PHB synthase (phbC) gene from *Z. ramigera* into the chromosome of *E. coli* and other Gram-negative bacteria.
Figure 6A:
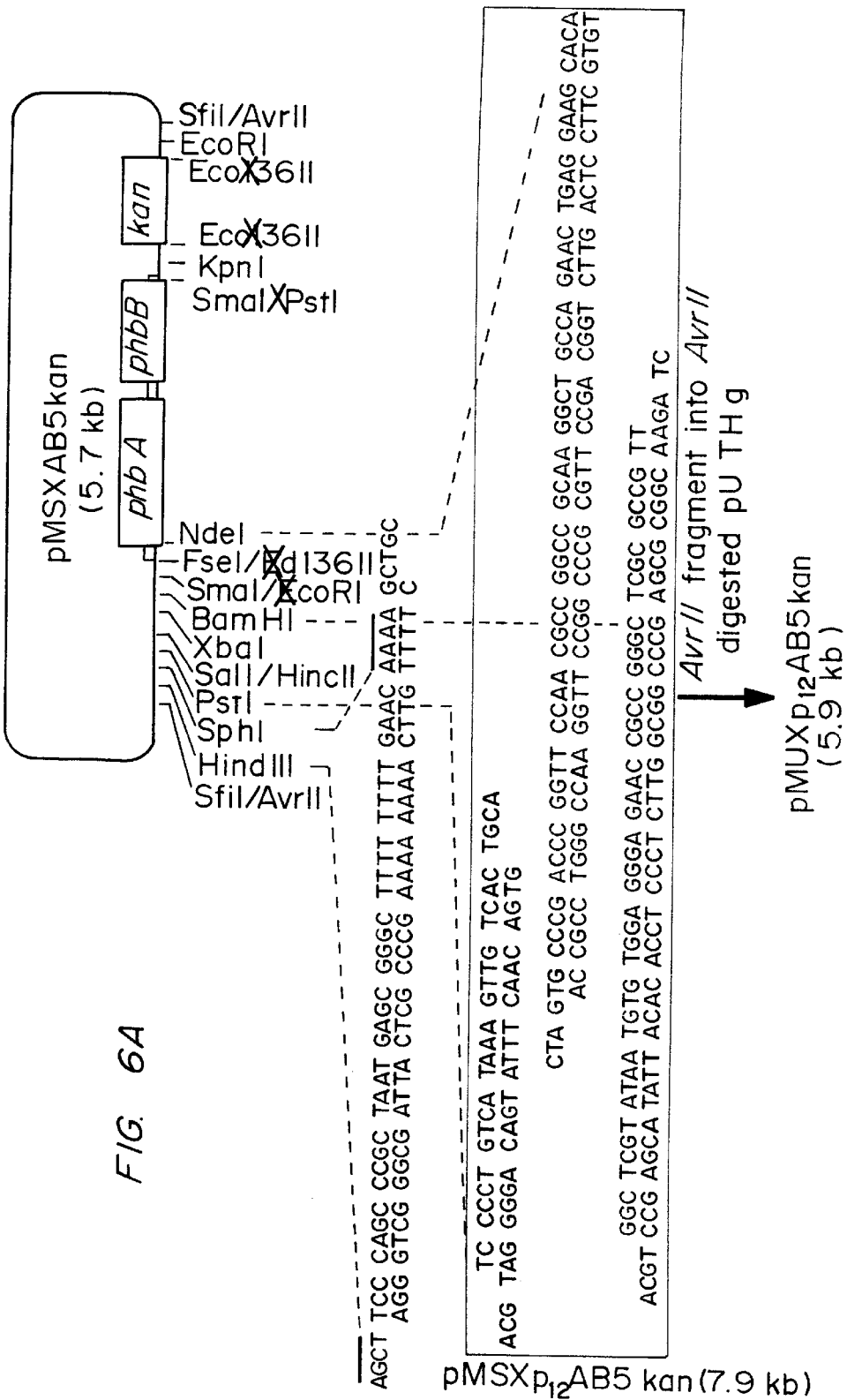

Plasmid pMUXC$_5$cat contains the phbC gene from *Z. ramigera* on a transposable element for integration of this gene on the chromosome of a recipient strain (FIG. 5). Strong translational sequences were obtained from pKPS4 which encodes PHA synthase encoding phaCl from *P. oleovorans* in the pTrc vector (Pharmacia). In this construct, phaCl is preceded by a strong ribosome binding site: AGGAGGTTTTT(-ATG) (SEQ ID NO: 4). The phaCl gene, including the upstream sequences, was cloned as a blunt ended EcoRI-HindIII fragment in the SmaI site of pUC18Sfi to give pMSXC$_3$. A blunt ended cat gene cassette was subsequently cloned in the blunt-ended Sse8387II site, resulting in pMSXC$_3$cat. At this point, all of the phaCl coding region except the 5' 27 base pairs were removed as a PstI-BamHI fragment and replaced by the corresponding fragment from the phbC gene from *Z. ramigera*. The resulting plasmid, pMSXC$_5$cat, encodes a hybrid PHB synthase enzyme with the 9 amino terminal residues derived from the *P. oleovorans* PHA synthase and the remainder from *Z. ramigera*. The C$_5$cat cassette was then excised as an AvrII fragment and cloned in the corresponding sites of pUTHg, thereby deleting the mercury resistance marker from this vector. The resulting plasmid, pMUXC$_5$cat, contains a C$_5$cat mini-transposon in which phbC is not preceded by a promoter sequence. Expression of the cassette upon integration is therefore dependent on transcriptional sequences that are provided by the DNA adjacent to the integration site.

pMSXTp$_1$AB$_5$kan2 was constructed from pMSXTp$_1$kan as follows (FIG. 6). First pMSXTp$_1$kan was digested with NdeI, filled in with Klenow and religated to obtain pMSXTp$_1$kan2 in which the NdeI site is deleted. This deletion results in a unique NdeI site just upstream of phbA of *Z. ramigera* during later stages of the cloning procedure.

B$_5$ was cloned as a NarI fragment from pZT1 and cloned in the HincII site of pUC18Sfi to generate pMSXB$_5$. A$_5$ was inserted as an FseI/blunt-SalI fragment in the Ecl136II-SalI sites resulting in pMSXAB$_5$ and regenerating the *Z. ramigera* AB$_5$ intergenic region. pMSXAB$_5$cat was created by inserting a promoterless cat cassette in the HindIII site of pMSXAB$_5$. The AB$_5$ fragment from pMSXAB$_5$cat was cloned as a EcoRI-PstI fragment into the SmaI site of pMSXTp$_1$kan2 giving pMSXTp$_1$AB$_5$kan2.

Expression of phbAB5 was improved by introduction of a strong promoter upstream of these genes (FIG. 6). This promoter was generated with sets of oligonucleotides that provide upstream activating sequences, a −35 promoter region, a −10 promoter region with transcriptional start site(s), and mRNA sequences with possible stabilizing functions. Plasmid pMSXTp$_1$AB$_5$kan2 was digested with PstI/XbaI and a fragment containing the −10 region of the lac promoter was inserted as a fragment obtained after annealing oligonucleo-tides 3A
(5'GGCTCGTATAATGTGTGGAGGGAGAACCGCCGGGCTCGCGCCGTT)
(SEQ ID NO:5)

and 3B
(5'CTAGAACGGCGCGAGCCCGGCGGTTCTCCCTCCACA
CATTATACGA GCCTGCA)
(SEQ ID NO:6).

Next, a fragment containing a consensus *E. coli* pho box and −35 promoter region were inserted into the PstI site as a fragment obtained after annealing the oligonucleotides:

2A:
(5' TCCCC TGTCATAAAGTTGTCACTGCA)       (SEQ ID NO:7)

and 2B
(5' GTGACAACTTTATGACAGGGG ATGCA)       (SEQ ID NO:8).

Next, the messenger stabilizing sequence including the transcriptional start site from AB$_5$ was inserted into the XbaI-NdeI sites as a fragment obtained after annealing the oligonucleotides:

4A
(5': CTAGTGCCGG
ACCCGGTTCCAAGGCCGGCCGCAAGGCTGCCAGAACTGAGGAAG
CACA) (SEQ ID NO:9)

and 4B:
(5'TATGTGCTTCCTCAGTTCTGGCAGCCTTGCGGCCGGCCTTGGAA
CCGGGTCCGGCA) (SEQ ID NO:10).

The resulting plasmid is pMSXp$_{12}$AB$_5$kan2. The AvrII fragment, containing Tp$_{12}$AB$_5$kan2 was cloned into pUTHg cut with AvrII and used for integration into the genome of MBX379 and MBX245.

The $p_{12}AB_5$kan expression cassette were then excised as a 2.8 kb AvrII fragment and ligated into the AvrII site of pUTHg and transformed into *E. coli* strain CC118 λpir to obtain plasmids pMUXp$_{12}$AB$_5$kan. This plasmid was then transformed into *E. coli* S17-1 λpir and used to insert $p_{12}AB_5$kan expression cassettes into the chromosome of *E. coli* strains by conjugation (Herrero et al. J. Bacteriol. 1990, 172: 6557–6567).

Example 5
Integration of phb Genes into the Chromosome of *E. coli*.

Material and Methods

*E. coli* strains were grown in Luria-Bertani medium (Sambrook et. al., Molecular Cloning, a laboratory manual, 2nd Ed., Cold Spring Harbor Laboratory Press, Cold Spring Harbor, N.Y.) at 37° C. or 30° C. or in minimal E2 medium (Lageveen et al., Appl. Environ. Microbiol. 1988, 54: 2924–2932). DNA manipulations were performed on plasmid and chromosomal DNA purified with the Qiagen plasmid preparation or Qiagen chromosomal DNA preparation kits according to manufacturers recommendations. DNA was digested using restriction enzymes (New England Biolabs, Beverly, Mass.) according to manufacturers recommendations. DNA fragments were isolated from 0.7% agarose-Tris/acetate/EDTA gels using a Qiagen kit.

Plasmid DNA was introduced into *E. coli* cells by transformation or electroporation (Sambrook et al. Molecular Cloning, a laboratory manual, 2nd Ed., Cold Spring Harbor Laboratory Press, Cold Spring Harbor, N.Y.). Transposition of phb genes from the pUT vectors was achieved by mating of the plasmid donor strain and the recipient (Herrero et al. J. Bacteriol. (1990) 172: 6557). The recipient strains used were spontaneous naladixic acid or rifampicin resistant mutants of *E. coli* derived from either LS5218 or MBX23. MBX23 is LJ14 rpoS::Tn10 in which the rpoS::Tn10 allele was introduced by P1 transduction from strain 1106 (Eisenstark). Recipients in which phb genes have been integrated into the chromosome were selected on naladixic acid or rifampicin plates supplemented with the antibiotic resistance specified by the mini-transposon, kanamycin or chloramphenicol. Oligonucleotides were purchased from Biosynthesis or Genesys. DNA sequences were determined by automated sequencing using a Perkin-Elmer ABI 373A sequencing machine. DNA was amplified using the synthase-chain-reaction in 50 microliter volume using PCR-mix from Gibco-BRL (Gaithersburg, Md.) and an Ericomp DNA amplifying machine.

Accumulated PHA was determined by gas chromatographic (GC) analysis as follows. About 20 mg of lyophilized cell mass was subjected to simultaneous extraction and butanolysis at 110° C. for 3 hours in 2 mL of a mixture containing (by volume) 90% 1-butanol and 10% concentrated hydrochloric acid, with 2 mg/mL benzoic acid added as an internal standard. The water-soluble components of the resulting mixture were removed by extraction with 3 mL water. The organic phase (1 μL at a split ratio of 1:50 at an overall flow rate of 2 mL/min) was analyzed on an HP 5890 GC with FID detector (Hewlett-Packard Co, Palo Alto, Calif.) using an SPB-1 fused silica capillary GC column (30 m; 0.32 mm ID; 0.25 μm film; Supelco; Bellefonte, Pa.) with the following temperature profile: 80° C., 2 min; 10° C. per min to 250° C.; 250° C., 2 min. The standard used to test for the presence of 4-hydroxybutyrate units in the polymer was γ-butyrolactone, which, like poly(4-hydroxybutyrate), forms n-butyl 4-hydroxybutyrate upon butanolysis. The standard used to test for 3-hydroxybutyrate units in the polymer was purified PHB.

1-Methyl-3-nitro-1-nitroso-guanidine (NTG) mutagenesis was performed as described by Miller (A short course in bacterial genetics, Cold Spring Harbor Laboratory Press, Cold Spring Harbor, N.Y.) using a 90 minute treatment with 1 mg/ml NTG corresponding to 99% killing.

Results

C$_5$cat was introduced into the chromosome of MBX23 by conjugation using S17-1 λpir (pMUXC$_5$cat) the donor strain. The conjugation mixture was spread on LB/N1/Cm plates and integrants were obtained of which 40% were sensitive to ampicillin, indicating that no plasmid was present in these strains. Five integrants were transformed with pMSXAB$_5$cat (Ap$^r$) and grown on LB/Ap/Cm/2% glucose to examine biosynthetic activity of PHB synthase. MBX326 expressed the highest synthase activity and was used in further studies. Expression of PHB synthase was increased by restreaking MBX326 successively on LB plates containing 100, 200, 500 and 1000 μg/ml chloroamphenicol. Strain MBX379 is derived from MBX326 and exhibits chloramphenicol resitence up to 1000 μg/ml.

*E. coli* S17-1 λpir containing pMUXp$_{12}$AB$_5$kan was mated with MBX379. Transgenic strains in which phbAB$_5$kan had integrated on the chromosome were selected on LB/N1/Km plates. Among the integrants, PHB producers were identified on LB/glucose plates and MBX677 (MBX379:: p$_{12}$AB$_5$kan) was used for further studies. The PHB level in this strain grown in Luria-Bertani/2% glucose medium was 58% whereas 38% PHB was accumulated in minimal medium supplemented with 2% glucose.

Example 6
Mutagenesis of Transgenic *E. coli* Strains for Enhanced PHB Production Mutagenesis using NTG or EMS was used to improve PHB formation in MBX680. Strain MBX769 and MBX777 were selected after treatment of MBX680 with EMS and NTG respectively. These strains are able to grow on R2-medium supplied with 1% glucose, 0.5% corn steep liquor and 1 mg/ml chloramphenicol. MBX769 was grown in 50 ml R-10 medium/ 0.5% CSL with 2 or 3% glucose at 37° C. for 20 to 26 hours. PHB was accumulated to 71% of the cell dry weight. Similarly, MBX769 was grown in 50 ml LB with or without 0.375 g/L KH$_2$PO$_4$, 0.875 K$_2$HPO$_4$ and 0.25 (NH$_4$)$_2$SO$_4$ and a total of 50 g/L glucose (five aliquots were added over the course of the incubation). After 63 hours of incubation, PHB had accumulated up to 96% of the cell dry weight. PHB levels in MBX777 strain grown in Luria-Bertani/2% glucose medium was 67% whereas in minimal medium supplemented with 2% glucose 57% PHB was accumulated.

Improved transgenic *E. coli* strains with a chromosomal phbC gene were obtained by P1 transduction of the C5cat allele from MBX379 into LS5218, LS5218fadAB101::Tn10 and LS5218fadR$^+$zcf117::Tn10. The resulting strains are MBX816, MBX817 and MBX821, respectively.

Example 7
Poly(4-hydroxybutyrate) (P4HB) Synthesis in *E. coli* Using an Endogenous 4-Hydroxybutyryl-CoA Transferase Activity

*E. coli* contains an endogenous gene encoding an enzyme with 4-hydroxybutyryl-CoA transferase activity. Strains MBX821 and 1231 were grown in 250 ml Erlenmeyer flasks containing 50 to 100 ml 10% LB liquid medium with 4-hydroxybutyrate, alone or in combination with glucose, as carbon source. MBX1231 is a mutant of MBX821 obtained after treatment with 1-methyl-3-nitro-1-nitrosoguanidine and selected on plates containing 500 µg/ml chloramphenicol. Cultures were incubated at 32 to 33° C. with shaking at 200 rpm. Cultures were harvested after 24 hours of incubation and analyzed for PHA. Table x shows that these strains accumulate 2.5 to 3.5% of the cell dry weight as a P4HB homopolymer. P4HB formation in this strain is not dependent on a plasmid encoded PHB synthase nor a heterologously expressed 4-hydroxybutyryl-CoA transferase. When these strains are grown on solid media, P4HB levels are improved to around 11%.

| host | volume | rpm | 4HB | glc | T  | % LB | % PHA | F (4HB) |
|------|--------|-----|-----|-----|----|----|-------|---------|
| 821  | 100    | 200 | 5   | 2   | 32 | 10 | 2.5   | 1.0     |
| 1231 | 100    | 200 | 5   | 2   | 33 | 10 | 3.5   | 1.0     |
| 821  | on plate |   | 5   | 2   | RT | 10 | 10.5  | 1.0     |
| 1231 | on plate |   | 5   | 2   | RT | 10 | 11.5  | 1.0     |

Example 8
A Screening Method for Air Insensitive 4-hydroxybutyryl CoA Transferase The 4-hydroxybutyryl-CoA transferase from *C. kluyveri* appears to be inhibited by air, most likely by oxygen. Oxygen insensitive mutants can be screened for by growing mutants of an *E. coli* strain that harbors the 4-hydroxybutyryl-CoA transferase encoding hbcT gene on a plasmid and a PHA synthase gene on the chromosome, for P4HB synthesis under high oxygenation conditions and searching for white colonies (indicative of PHA accumulation) where the majority of the population forms grey colonies. Oxygen insensitive strains, MBX240 [pFS16], MBX379 [pFS16] and MBX830 [pFS16], were identified using this method. Populations of mutants can be generated in vivo by treating the original strain with chemical mutagens such as N-methyl-N'-nitro-N-nitrosoguanidine or ethylmethanesulfonate or with ultraviolet radiation. Alternatively, an hbcT containing plasmid can be mutagenized in vitro with hydroxylamine. Mutants expressing a functional 4-hydroxybutyryl-CoA transferase are then screened for on solid media or highly oxygenated liquid media for P4HB formation from 4-hydroxybutyrate.

Example 9
A Screening Method for Additional *E. coli* Genes Encoding 4-hydroxybutyryl CoA Biosynthetic Enzymes Expression of the enzymatic activity that converts 4HB to 4HB-CoA in MBX821 or 1231 may be elevated by mutagenesis. Appearance of P4HB in MBX821 and 1231 grown on solid media took approximately 150 hours. Mutants with improved P4HB accumulation characteristics can be screened for after random mutagenesis of these strains with chemical mutagens such as N-methyl-N'-nitro-N-nitrosoguanidine or ethylmethanesulfonate or with ultraviolet radiation. Desired mutants form white colonies within 2 to 5 days of incubation in the presence of 4-hydroxybutyrate.

Example 10
A Screening Method for Other Genes Encoding 4-hydroxybutyryl CoA Biosynthetic Enzymes Because applications involving plant systems require DNA with a high GC content, alternative 4-hydroxybutyryl CoA biosynthetic genes need to be identified and isolated. The low GC content of the hbcT gene would makes it a useful probe for identification and isolation of homologous genes from other AT-rich DNA containing microorganisms. HbcT genes with a high GC content however will not be identified by this method. *E. coli* strains that have a chromosomally integrated phbC gene encoding PHA synthase can be used to screen for such genes. For applications where genes are introduced into plants it is desirable to use DNA with a high GC content (Perlak F. J. et al., Proc. Natl. Acad. Sci. USA (1991) 88: 3324). When hbcT genes are expressed in *E. coli* MBX379 for instance, this strain is able to produce a P4HB polymer on agar plates containing 4-hydroxybutyrate in addition to the common nutrients. The formation of P4HB gives the colony an easily distinguishable white phenotype. Thus, gene libraries of PHB-co-4HB producing organisms. such as *R. eutropha, A. latus, P. acidovorans, C. testosteroni* and others are introduced into MBX379 or similar strains and directly plated on 4HB containing growth medium. White colonies are selected and the composition of the accumulated PHA is determined. Gene libraries are readily constructed from organisms of choice by isolating genomic DNA and cloning a representative collection of DNA fragments in plasmid vectors. Representative libraries should have 5,000 to 100,000 individual colonies. Libraries are either made as a broad host range library in vectors such as pLAFR3 or as *E. coli* libraries in vectors such as pUC19, pBR322. Depending on the type of library and the method of introducing the library in the host of choice, the genomic DNA fragments are either large (17–30 kb) or relatively small (2–6 kb). Libraries are introduced into the screening strains by electroporation, transformation or conjugation, dependent on the host and the vector used.

In addition to alternative 4-hydroxybutyryl CoA transferases, acyl CoA synthetases able to utilize 4-hydroxybutyrate as a substrate will be isolated by this method. Examples of genes encoding enzymes with such general activities are fadD, involved in uptake of long-side chain fatty acids, atoDA, involved in uptake of acetoacetate and short side chain fatty acids, catE, involved in degradation of aromatics, aceAB, encoding succinyl CoA synthetase, acsA and acsB encoding acetyl CoA synthetases and homologs of such genes. Alternatively the substrate specificity of these enzymes may be expanded to include 4-hydroxybutyrate by introducing plasmids with randomly mutagenized acyl CoA synthetase or transferase genes. Alternatively, the ygfH gene from *E. coli* which shares significant homology with the hbcT gene from *C. kluyveri* may be explored for 4-hydroxybutyryl CoA activity.

Figure 7:
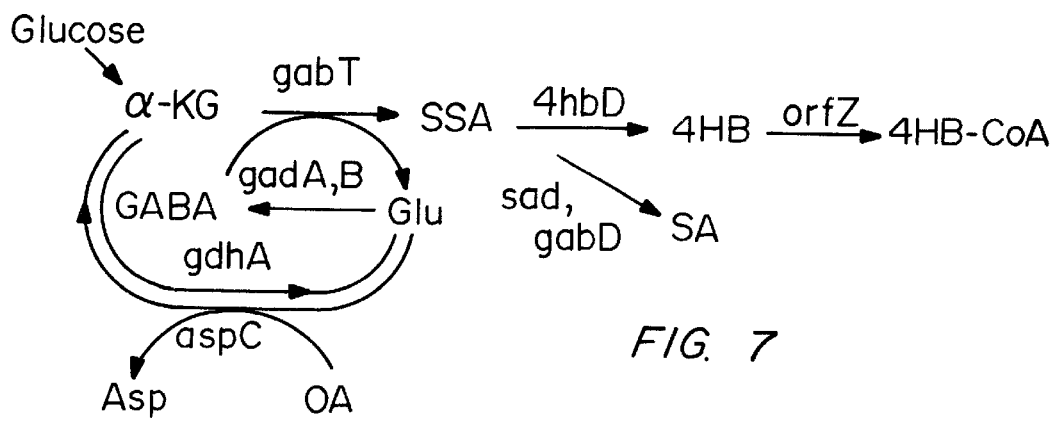
FIG. 7 is a schematic of the metabolic and genetic representation of the engineered biosynthetic pathway for 4-hydroxybutyryl-CoA synthesis. The gene products of gabT, 4hbD and hbcT are required for this pathway, gadAB and gdhA are helpful, whereas the gene products of aspC, sad and gabD are preferably absent or inactive.

Example 11
Endogenous Synthesis of 4HB-CoA from α-ketoglutarate

α-Ketoglutarate is a cellular metabolite that can be converted to 4HB as shown in FIG. 7. The pathway consists of a cyclic reaction catalyzed by the gabT, gadA/gadB and gdhA gene products. Formation of succinic acid semialdehyde from this cycle is favored once the product is further converted to 4HB-CoA by 4-HB dehydrogenase and 4HB-CoA transferase, and polymerized into a PHA by PHA synthase.

For this purpose the following plasmids were constructed in pMSXcat:

| 1. | pMSX-TD | hbcT-4hbD |
|---|---|---|
| 2. | pMSX-ABT | gdhA-gadB-gabT |
| 3. | pMTX-DBTT | 4hbD-gadB-gabT-hbcT |
| 4. | PMSX-ABTTD | gdhA-gadA-gabT-hbcT-4hbD |

1. 4hbD was obtained from pCK3 by PCR using the primers:

```
                                            (SEQ ID NO:11)
4HBD-N:   5'CTCTGAATTCAAGGAGGAAAAAATATGAAGTTAT
                   TAAAATTGGC (EcoRI)

(SEQ ID NO:12)
4HBD-C:   5'TTTCTCTGAGCTCGGGATATTTAATGATTGTAGG
                   (SacI).
```

Figure 8:
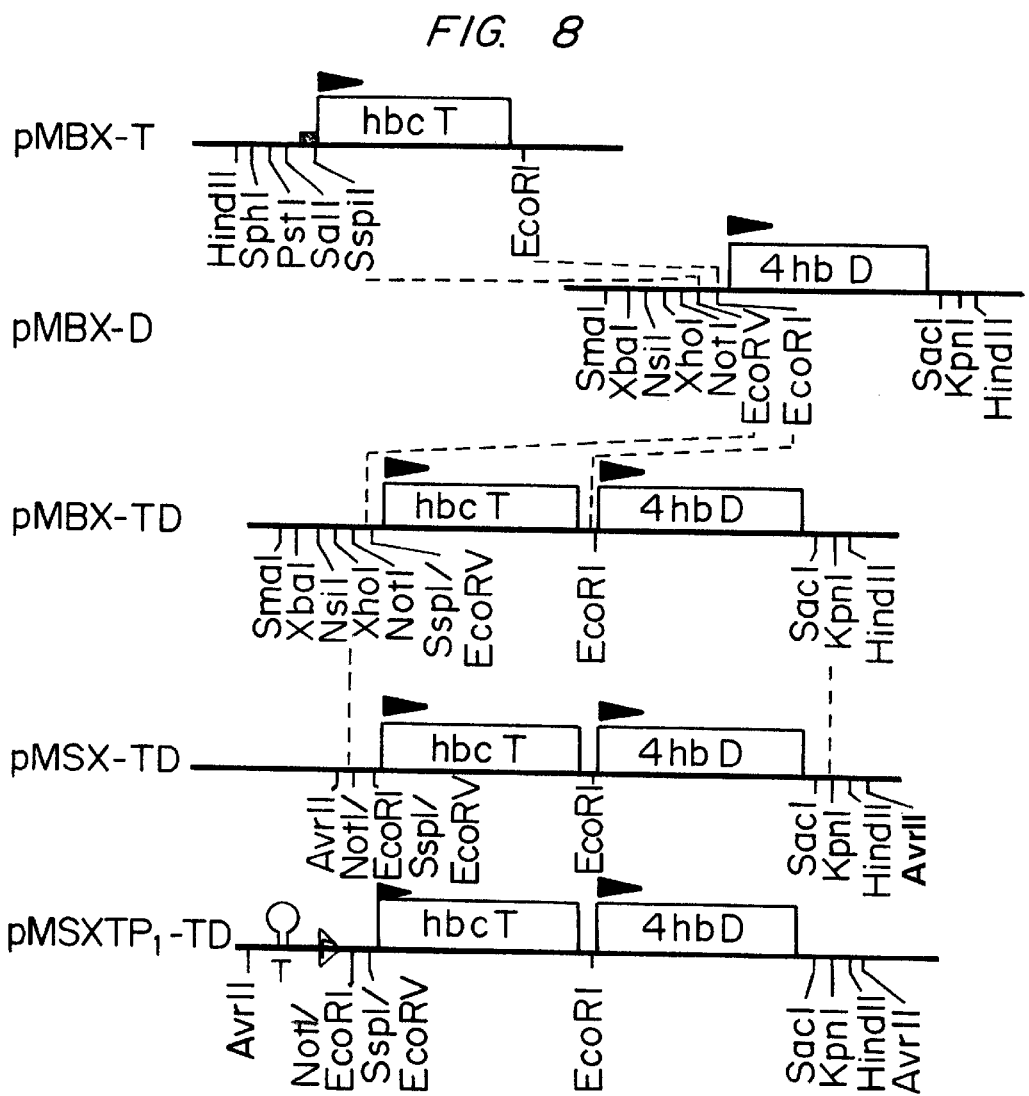
FIG. 8 is a schematic of the construction of plasmids pMSX-TD and pMSXTp1-TD, which expresses enzymes to convert α-ketoglutarate to 4-hydroxybutyryl-CoA.

The PCR product was cloned into pCR2.1 (pMBX-D). hbcT was cloned as an SspI-EcoRI fragment from pCK3 and cloned in EcoRV/EcoRI digested pMBX-D to give pMBX-TD. The artificial hbcT-4hbD operon was excised from pMBX-TD as a NotI-KpnI fragment and ligated into these sites in pUC18Sfi or pMSX-TP1 (pMSX-TD and pMSX-TP$_1$TD respectively) (FIG. 8). The TD or TP$_1$-TD fragment was excised as a AvrII fragment and ligated into AvrII digested pUTkan (pMUX-TD and pMUX-TP$_1$-TD). This plasmid allows random insertion of the TD/TP1-TD construct in the chromosome of E. coli. Expression of integrated TD is driven by an endogenous promoter whereas expression of integrated TP$_1$-TD is driven by P$_1$. Recombinants in which the construct had integrated were selected for their ability to grow on 4-hydroxybutyrate as sole carbon source. No antibiotic resistance marker was required to select the desired insertions.

Other genes encoding enzymes that facilitate conversion of succinic semialdehyde to 4-hydroxybutyryl CoA can be isolated routinely by complementation. After introduction of 4hbD homologs such genes confer on wild-type E. coli strains the ability to use 4HB as sole carbon source.

2. An operon consisting of gdhA-gadA-gabT was created in plasmid pUC18Sfi and inserted in the E. coli chromosome using the pUTkan vector. Recipients of the construct were isolated on E2/glycerol/_γ-hydroxybutyrate/N1 plates. Because the recipient strain is unable to use γ-hydroxybutyrate as nitrogen source (due to a gabT mutation), only those strains that express the operon grow on this medium. The gdhA gene was obtained from the E. coli chromosome using PCR and the following primers:

```
                                            (SEQ ID NO:13)
GH-Up:  5' AACGAATTCAATTCAGGAGGTTTTTATGGATCAGAC
           ATATTCTCTGGAGTC (EcoRI)

(SEQ ID NO:14)
GH-Dn:  5' TTGGGAGCTCTACAGTAAGAAATGCCGTTGG (SacI).
```

The gadB gene was obtained from the E. coli chromosome using PCR and the following primers:

```
                                            (SEQ ID NO:15)
GB-Up: 5' TAAGAGCTCAATTCAGGAGGTTTTTATGGATAAGAA
          GCAAGTAACGGATTTAAGG (SacI)

(SEQ ID NO:16)
GB-Dn: 5' TTCCCGGGTTATCAGGTATGCTTGAAGCTGTTCTGT
          TGGGC (XmaI).
```

The gabT gene was obtained from the E. coli chromosome using PCR and the following primers:

```
                                            (SEQ ID NO:17)
GT-Up:   5' TCCGGATCCAATTCAGGAGGTTTTTATGAACAGCAA
            TAAAGAGTTAATGCAG (BamHI)

(SEQ ID NO:18)
GT-Dn:   5' GATTCTAGATAGGAGCGGCGCTACTGCTTCGCC
            (XbaI).
```

DNA sequence information used to design the above primers was from GenBank, accession numbers: K02499 (gdhA), M84025 and X71917 (gadB), M88334 (gabT).

Figure 9:
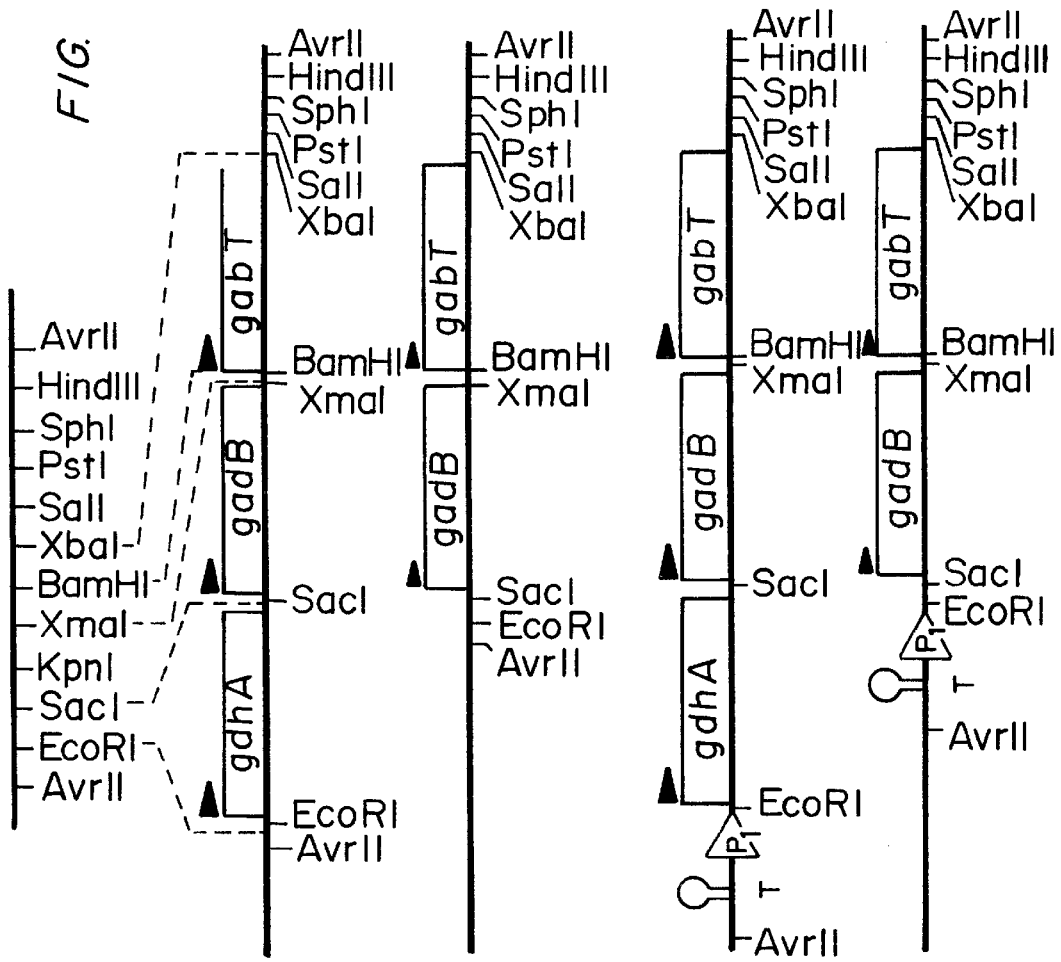
FIG. 9 is a schematic of the construction of plasmids pMSX-ABT, pMSXTp1-ABT and pMSXTp1-BT, which expresses enzymes to convert α-ketoglutarate to 4-hydroxybutyryl-CoA.

The three PCR products were digested with the indicated enzymes and sequentially cloned in the pUC18Sfi vector (pMSX-ABT) (FIG. 9). The operon was excised as an EcoRI-SalI fragment and cloned in pMSXTP$_1$ (pMSX-TP$_1$-ABT). Either the ABT or TP$_1$-ABT insert was moved to pUTkan to allow insertion of the gdhA-gadA-gabT operon in the chromosome of a gabT mutant of E. coli MBX245. Successful insertions were selected on E2/glycerol/γ-hydroxybutyrate /N1 plates.

Because gabT expression allows the use of γ-hydroxybutyrate as nitrogen source, genes that express this function can be easily selected for on minimal medium plates in which γ-hydroxybutyrate serves as the only nitrogen source. Expression of gabT at the end of the operon necessitates the transcription of the upstream genes for which no direct selection is available.

Glutamate dehydrogenase functions in this pathway as a source to provide glutamate in catalytic amounts. If sufficient glutamate is present, additional GdhA activity may not be required and incorporation of this gene in the described constructs is therefore optional.

3. The operons described under 1 and 2 were combined as follows: pMSX-TD was digested with KpnI, T4 polymerase treated and digested with XhoI; pMSX-ABT or pMSX-BT were digested with HindIII, Klenow treated and digested with SalI; the purified TD fragment was subsequently ligated into the prepared pMSX-ABT and pMSX-BT plasmids (FIG. 9).

Example 12

Endogenous Synthesis of 4HBCoA from GABA Precursors

Figure 10:
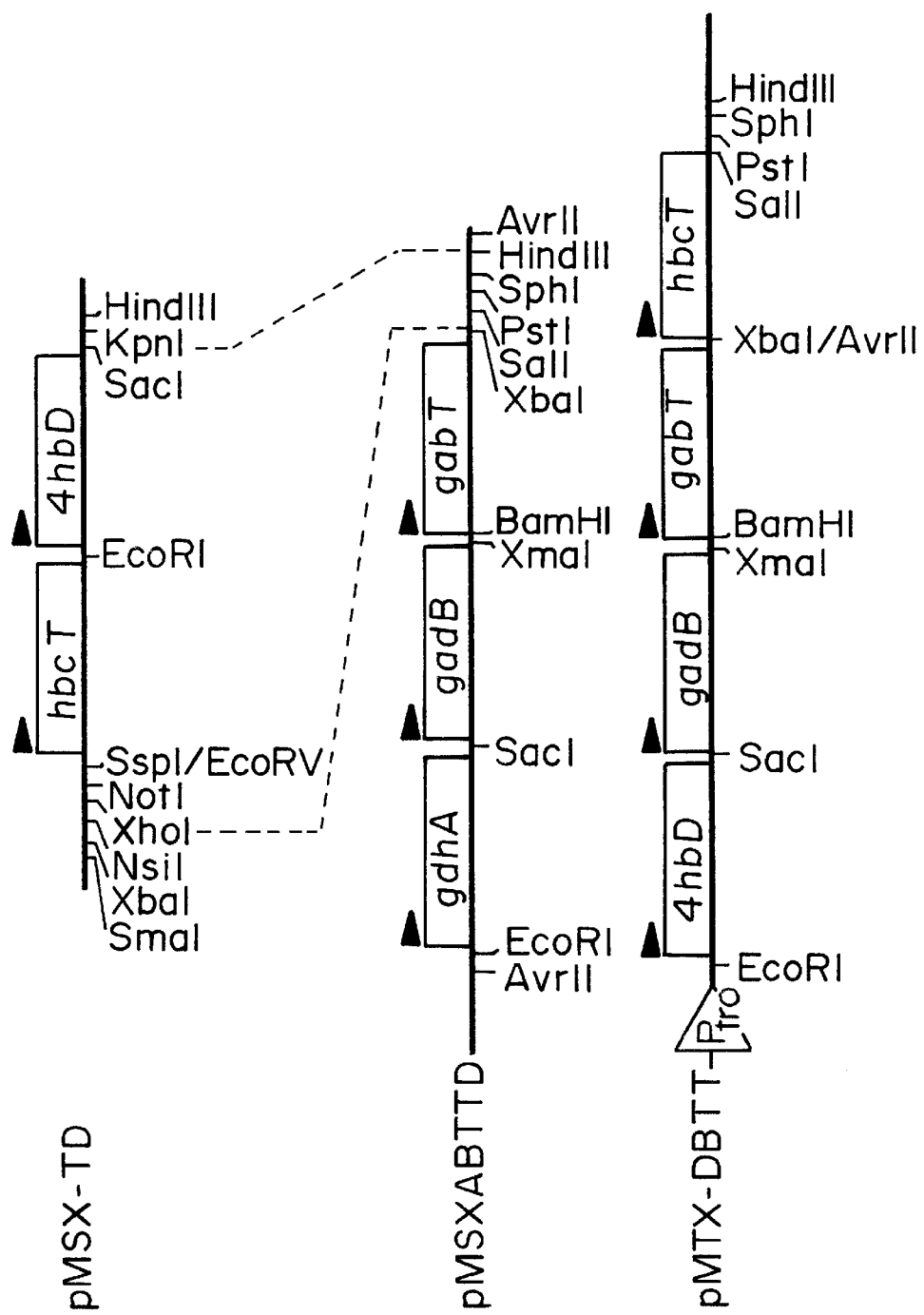
FIG. 10 is a schematic of the construction of plasmid pMSX-ABT and pMSX-ABT-TD which expresses enzymes to convert α-ketoglutarate to 4-hydroxybutyryl-CoA.

The common metabolite GABA is derived from glutamate and is normally metabolized via succinic semialdehyde to succinate in central metabolism. It may be desirable to improve the pathways to GABA to achieve high levels of the intermediates for P4HB formation. Besides the direct conversion of α-ketoglutarate to glutamate by glutamate dehydrogenase, this conversion is also part of many transamination reactions for instance with substrates such as glutamine and other amino acids, or putrescine. Recombinant and mutant organisms that overproduce arginine (the precursor of putrescine), glutamine or proline, consequently have increased levels of glutamate and GABA which can be shunted to 4HB-CoA with gabT, 4hbD and hbcT as described above (FIG. 10).

Example 13

Endogenous Synthesis of 4HBCoA from Succinate

Figure 4:
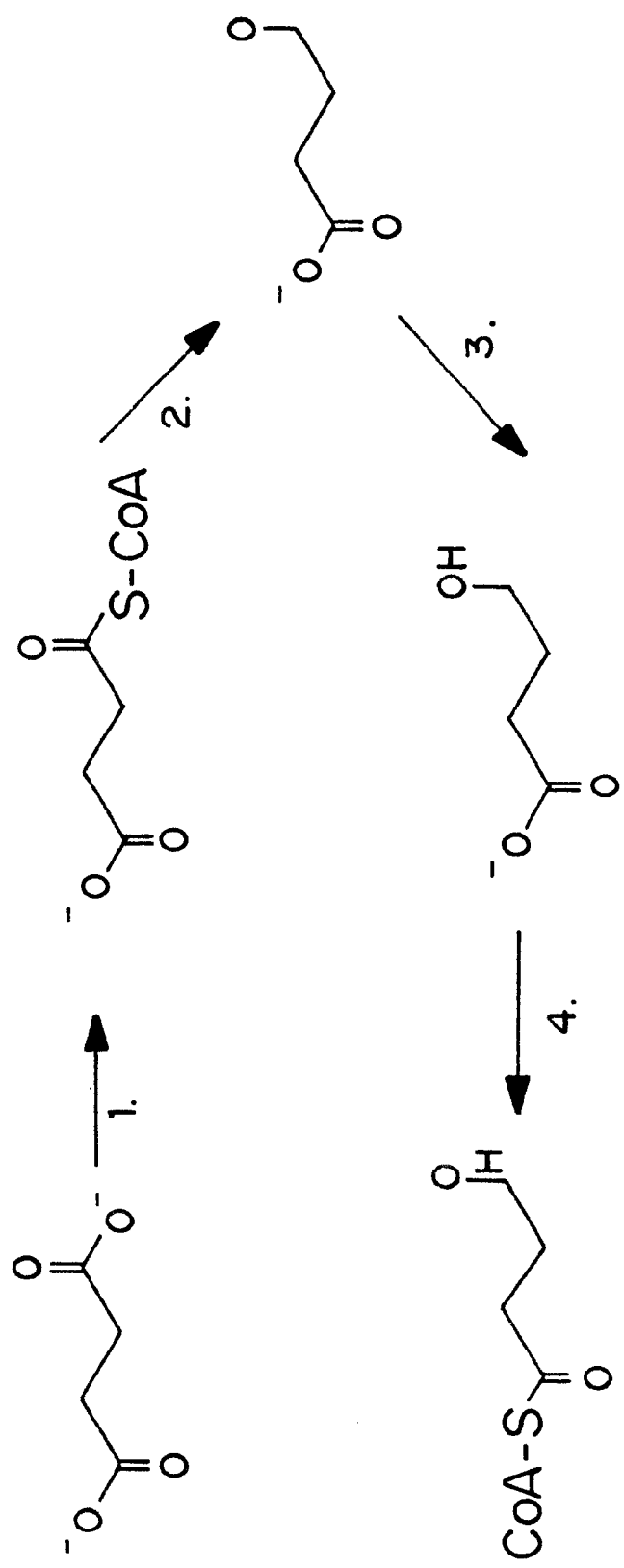
FIG. 4 is a schematic of the endogenous synthesis of 4-hydroxybutyryl CoA from succinate. 1. succinyl CoA-CoA transferase; 2. succinate semialdehyde dehydrogenase; 3. 4-hydroxybutyrate dehydrogenase; 4. 4-hydroxybutyryl CoA transferase.

HbcT is not required for E. coli to grow on 4-hydroxybutyrate when cat1, 4hbD and sucD are introduced (Söhling and Gottschalk, 1996, J. Bacteriol. 178, 871–880) possibly because the reverse action of SucD, 4HBD and Cat1 converts 4HB to succinate, a central metabolite in E. coli. In principle, these genes together allow the conversion of succinate to 4-HB. The pathway as depicted in FIG. 4 can then be assembled from the cat1, sucD, 4hbD and hbcT genes of *C. kluyveri*. Alternatively, these genes can be isolated from other Clostridium species such as *C. aminobutyricum*. Although *E. coli* does have a succinyl-CoA:CoA transferase itself (sucCD; Mat-Jan et al. Mol. Gen. Genet. (1989) 215: 276–280), it is desirable to introduce this gene from another source because this activity is not prominent in *E. coli* (Amarasingham and Davis, J. Biol. Chem. (1965) 240: 3664–3668). Alternatively, expression of the *E. coli* gene can be optimized for the current application.

Figure 11:
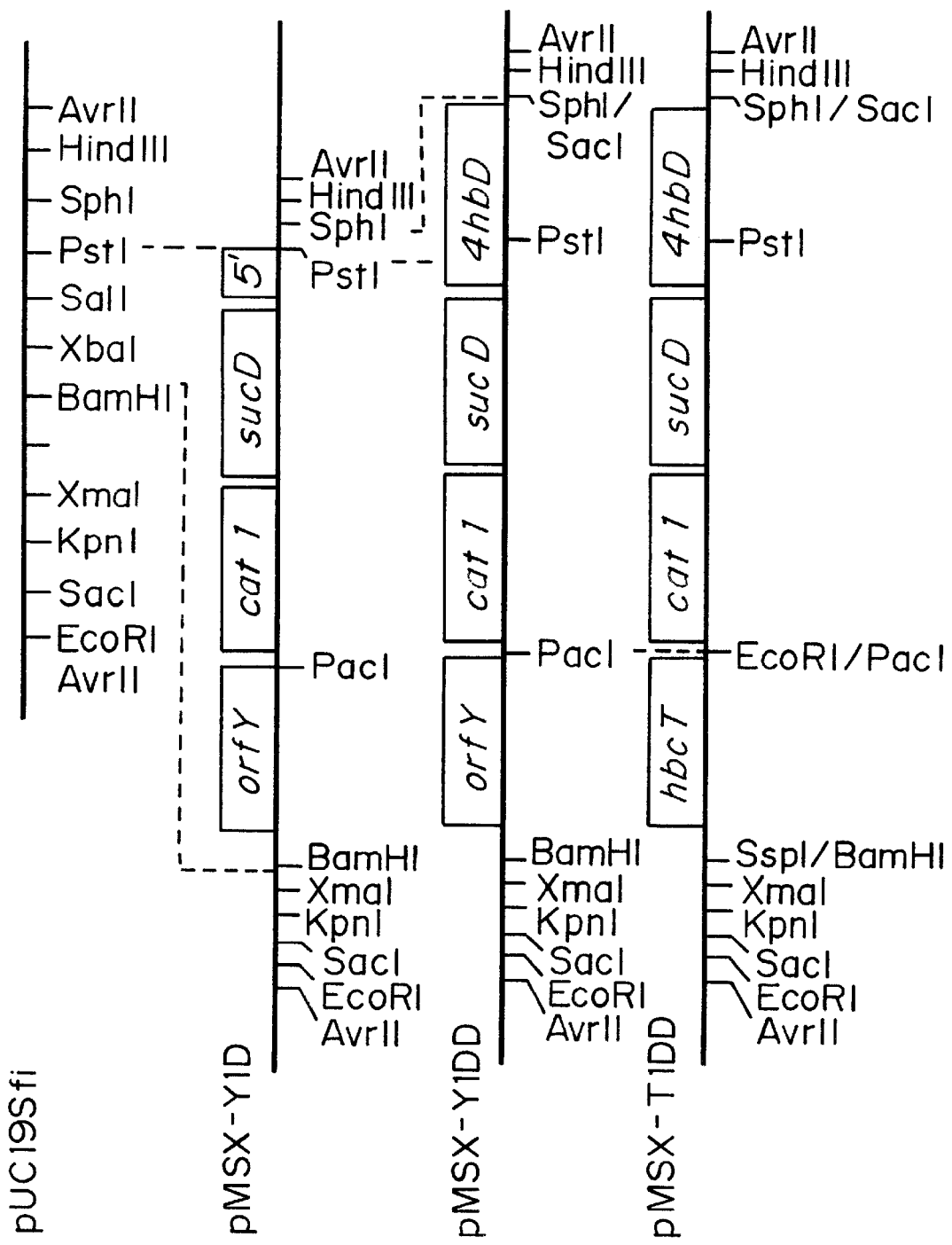
FIG. 11 is a schematic of the construction of plasmid pMSX-T1DD which expresses enzymes to convert succinate to 4-hydroxybutyryl-CoA

An operon was constructed for integration in the *E. coli* chromosome consisting of hbcT-catI-sucD-4hbD. Strains in which integration was successful are able to grown on 4HB if 4hbD is expressed (Söhling and Gottschalk, 1996, J. Bacteriol. 178, 871–880). The construction of this operon proceeded as follows (FIG. 11):

A BamHI-PstI fragment from pCK3 containing orfY, catI, sucD and the 5' end of 4hbD was ligated in the corresponding sites of pMSXcat (pMSX-Y1D). The 4hbD gene was completed by inserting the PstI-SacI fragment of pMSX-D in PstI-SphI digested pMSX-Y1D (pMSX-Y1DD). To achieve this, both fragments in this ligation were T4 polymerase treated after the SphI and SacI digestions to create blunt ends before an additional PstI digestion was started. OrfY in pMSX-Y1DD was replaced with hbcT by digesting pMSX-Y1DD with BamHI and PacI, followed by blunt ending the fragment with Klenow/T4 polymerase and dephosphorylation, and then ligation of the SspI/EcoRI, Klenow treated hbcT fragment into this vector (pMSX-T1DD). A fragment providing the regulatory sequences, terminator and promoter was inserted as a blunt ended fragment in the SmaI site of pMSX-T1DD. An integration plasmid for this operon was constructed by cloning the insert of pMSX-T1DD as an SfiI fragment into pUTkan.

Example 14
Improved Endogenous Synthesis of 4HBCoA

In order to prevent drainage of intermediates from these new pathways, it may be desirable to inactivate the genes encoding aspartate transaminase (aspC) and the NADP and NAD dependent succinic semialdehyde dehydrogenases (sad and gabD). Mutations in the individual genes were obtained from different sources: A strain containing the aspC13I mutation is obtained from the *E. coli* Genetic Stock Center as strain CGSC5799. The aspC gene maps to minute 21.1 and is therefore linked to the Tn10 (Tc) marker in CAG12094 (zcc-282 at 22.25 minutes) or CAG18478 (zbj-1230 at 20.00 minutes) and to the Tn10 Km marker in CAG12130 (zcb-3111 at minute 21.00). No mutations in the gabD gene are known and deletion of this activity can be achieved by cloning the gene by PCR, insertion of a genetic marker such as antibiotic resistance, integration using recBC strains or vectors constructed for this purpose such as pMAK705 and finally, bacteriophage P1 transduction to transfer the gene to the desired host.

Example 15
Expression of A PHA Synthase and 4-hydroxybutyryl-CoA Transferase in Oilseed Crops.

Methods for the identification of genes encoding enzymes capable of forming 4-hydroxybutyryl-CoA from 4-hydroxybutyric acid (i.e., having 4-hydroxybutyryl-CoA transferase activity) which can be expressed in a transgenic plant comprising a PHA synthase transgene were developed by standard procedures. In certain cases, it may also be useful to express other PHA biosynthetic genes such as a β-ketothiolase and/or acetoacetyl-CoA reductase in the plant crop of interest. Methods for expressing a PHA synthase transgene in an oilseed crop have been described (U.S. Pat. Nos. 5,245,023 and 5,250,430; 5,502,273; 5,534,432; 5,602,321; 5,610,041; 5,650,555: 5,663,063; WO, 9100917, WO 9219747, WO 9302187, WO 9302194 and WO 9412014, Poirier et. al., 1992 Science 256; 520–523, Williams and Peoples, 1996 Chemtech 26, 38–44) all of which are incorporated herein by reference. In order to achieve this goal, it is necessary to transfer a gene, or genes in the case of a PHA synthase with more than one subunit, encoding a PHA synthase from a microorganism into plant cells and obtain the appropriate level of production of the PHA synthase enzyme. In addition it may be necessary to provide additional PHA biosynthetic genes, eg. an acetoacetyl-CoA reductase gene, a 4-hydroxybutyryl-CoA transferase gene or other genes encoding enzymes required to synthesize the substrates for the PHA synthase enzymes. In many cases, it is desirable to control the expression in different plant tissues or organelles using methods known to those skilled in the art (Gasser and Fraley, 1989, Science 244; 1293–1299; Gene Transfer to Plants (1995), Potrykus, I. and Spangenberg, G. eds. Springer-Verlag Berlin Heidelberg New York. and "Transgenic Plants: A Production System for Industrial and Pharmaceutical Proteins" (1996), Owen, M. R. L. and Pen, J. eds. John Wiley & Sons Ltd. England) all of which are incorporated herein by reference. U.S. Pat. No. 5,610,041 describes plastid expression by adding a leader peptide to direct the protein expressed from the nuclear gene to the plastid. More recent technology enables the direct insertion of foreign genes directly into the plastid chromosome by recombination (Svab et. al., 1990, Proc. Natl;. Acad. Sci. USA. 87: 8526–8530; McBride et. al., 1994, Proc. Natl. Acad Sci. USA. 91: 7301–7305). The prokaryotic nature of the plastid RNA and protein synthesis machinery also allows for the expression of microbial operons such as for example the phbCAB operon of *A. eutrophus*. This technology allows for the direct incorporation of a series of genes encoding a multi-enzyme pathway into the plastid genome. It is also important to take into account the importance of 5'-untranslated regions of plastid genes for mRNA stability and translation (Hauser et. al., 1996. J. Biol. Chem. 271: 1486–1497). In some cases it may be useful to re-engineer the 5'-untranslated regions, remove secondary structure elements, or add elements from highly expressed plastid genes to maximize expression of transgenes encoded by an operon.

We claim:

1. A recombinant host having stably incorporated into the genome a gene encoding a heterologous enzyme selected from the group consisting of a polyhydroxyalkanoate synthase and a 4-hydroxybutyrate-CoA (4HB-CoA2) transferase, wherein when the host is provided with feedstock selected from the group consisting of carbohydrates, succinate, 4-hydroxybutyrate, α-ketoglutarate, and amino acids, the enzyme is expressed in a sufficient amount to produce polyhydroxybutyrate-co-polyhudrohexanoate or poly 4-hydroxybutyrate.

2. The host of claim 1 having stably incorporated into its genome both a polyhydroxyalkanoate synthase and a 4HB-CoA transferase.

3. The host of claim 1 wherein the host is E. coli.

4. The host of claim 3 wherein the heterologous enzyme is a polyhydroxyalkanoate synthase and the host expresses an endogenous enzyme with 4HB-CoA transferase activity.

5. The host of claim 1 further comprising genes expressing enzymes selected from the group consisting of β-ketothiolase and acetoacetyl CoA reductase.

6. A method for enhancing production of polymers containing 4HB in a host comprising stably incorporating into the genome of the host a gene encoding a heterologous enzyme selected from the group consisting of a polyhydroxyalkanoate synthase and a 4HB-CoA transferase;

providing the host with feedstock selected from the group consisting of carbohydrates, succinate, 4-hydroxybutyrate, α-ketoglutarate, and amino acids.

wherein the enzyme is expressed in a sufficient amount to produce polyhydroxybutyrate-co-polybydroxyhexanoate or poly 4-hydroxybutyrate.

7. The method of claim 6 wherein the host has stably incorporated into its genome both a polyhydroxyalkanoate synthase and a 4HB-CoA transferase.

8. The method of claim 6 further comprising enhancing expression of the heterologous enzyme.

9. The method of claim 8 wherein expression is enhanced by mutating the host followed by providing 4HB as a substrate and screening for polymer production by the mutated host.

10. The method of claim 6 further comprising providing a host expressing enzymes selected from the group consisting of α-ketoglutarate transaminase, glutamate-succinic semialdehyde transaminase, glutamate dehydrogenase, glutamate decarboxylase, 4-hydroxybutyrate dehydrogenase and 4-hydroxybutyryl CoA transferase.

11. The method of claim 6 further comprising providing a host expressing enzymes degrading arginine, glutamine or proline to produce gamma amino butyric acid.

12. A 4HB polymer produced by a recombinant host having stably incorporated into the genome a gene encoding a heterologous enzyme selected from the group consisting of a polyhydroxyalkanoate synthase and a 4HB-CoA transferase.

13. A vector comprising, an isolated gene encoding a 4HB-CoA transferase under the control of a promoter for enhancing expression, wherein expression occurs after integration into the genome of a heterologous host.

* * * * *

UNITED STATES PATENT AND TRADEMARK OFFICE
CERTIFICATE OF CORRECTION

PATENT NO. : 6,689,589 B2
DATED : February 10, 2004
INVENTOR(S) : Gjalt W. Huisman et al.

It is certified that error appears in the above-identified patent and that said Letters Patent is hereby corrected as shown below:

Column 31,
Lines 36-46, please replace Claim 1 with the following Claim 1:

1. A recombinant host having stably incorporated into the genome a gene encoding a heterologous enzyme selected from the group consisting of a polyhydroxyalkanoate synthase and a 4-hydroxybutyrate-CoA (4HB-CoA) transferase, which is expressed in the host, wherein the host is provided with feedstock selected from the group consisting of carbohydrates, succinate, 4-hydroxybutyrate, alpha-ketoglutarate, and amino acids, the host produces polyhydroxybutyrate-co-polyhydroxyhexanoate or poly 4-hydroxybutyrate.

Column 31, line 57 - Column 32, line 37,
Please replace Claim 6 with the following Claim 6:
6. A method for enhancing production of polymers containing 4HB in a host comprising:
    stably incorporating into the genome of the host a gene encoding a heterologous enzyme selected from the group consisting of a polyhydroxyalkanoate synthase and a 4HB-CoA transferase, wherein the enzyme is expressed by the host; and
    providing the host with feedstock selected from the group consisting of carbohydrates, succinate, 4-hydroxybutyrate, a-ketoglutarate, and amino acids,
    wherein the host produces polyhydroxybutyrate-co-polyhydroxyhexanoate or poly 4-hydroxybutyrate.

Signed and Sealed this

Twenty-third Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,689,589 B2
DATED : February 10 ,2004
INVENTOR(S) : Gjalt W. Huisman et al.

It is certified that error appears in the above-identified patent and that said Letters Patent is hereby corrected as shown below:

Column 31,
Lines 36-46, please replace Claim 1 with the following Claim 1:

1. A recombinant host having stably incorporated into the genome a gene encoding a heterologous enzyme selected from the group consisting of a polyhydroxyalkanoate synthase and a 4-hydroxybutyrate-CoA (4HB-CoA) transferase, which is expressed in the host, wherein the host is provided with feedstock selected from the group consisting of carbohydrates, succinate, 4-hydroxybutyrate, alpha-ketoglutarate, and amino acids, the host produces poly(3-hydroxybutyrate-co-4-hydroxybutyrate) or poly(4-hydroxybutyrate).

Column 31, line 57 - Column 32, line 37,
Please replace Claim 6 with the following Claim 6:
6. A method for enhancing production of polymers containing 4HB in a host comprising:
    stably incorporating into the genome of the host a gene encoding a heterologous enzyme selected from the group consisting of a polyhydroxyalkanoate synthase and a 4HB-CoA transferase, wherein the enzyme is expressed by the host; and
    providing the host with feedstock selected from the group consisting of carbohydrates, succinate, 4-hydroxybutyrate, a-ketoglutarate, and amino acids,
    wherein the host poly(3-hydroxybutyrate-co-4-hydroxybutyrate) or poly(4-hydroxybutyrate).

Signed and Sealed this

Eighteenth Day of October, 2005

JON W. DUDAS
*Director of the United States Patent and Trademark Office*

UNITED STATES PATENT AND TRADEMARK OFFICE
CERTIFICATE OF CORRECTION

PATENT NO.        : 6,689,589 B2
APPLICATION NO.   : 10/006915
DATED             : February 10, 2004
INVENTOR(S)       : Gjalt W. Huisman et al.

It is certified that error appears in the above-identified patent and that said Letters Patent is hereby corrected as shown below:

Column 31,
Lines 36-46, please replace Claim 1 with the following Claim 1:

1. A recombinant host having stably incorporated into the genome a gene encoding a heterologous enzyme selected from the group consisting of a polyhydroxyalkanoate synthase and a 4-hydroxybutyrate-CoA (4HB-CoA) transferase, which is expressed in the host, wherein the host is provided with feedstock selected from the group consisting of carbohydrates, succinate, 4-hydroxybutyrate, alpha-ketoglutarate, and amino acids, the host produces poly(3-hydroxybutyrate-co-4-hydroxybutyrate) or poly(4-hydroxybutyrate).

Column 31, line 57 - Column 32, line 37,
Please replace Claim 6 with the following Claim 6:
6. A method for enhancing production of polymers containing 4HB in a host comprising:
  stably incorporating into the genome of the host a gene encoding a heterologous enzyme selected from the group consisting of a polyhydroxyalkanoate synthase and a 4HB-CoA transferase, wherein the enzyme is expressed by the host; and
  providing the host with feedstock selected from the group consisting of carbohydrates, succinate, 4-hydroxybutyrate, -ketoglutarate, and amino acids,
  wherein the host produces polyhydroxybutyrate-co-polyhydroxyhexanoate or poly 4-hydroxybutyrate.

This certificate supersedes the Certificates of Correction issued November 23, 2004 and October 18, 2005.

Signed and Sealed this

Fourth Day of May, 2010

David J. Kappos
*Director of the United States Patent and Trademark Office*

SEQUENCE LISTING

<160> NUMBER OF SEQ ID NOS: 18

<210> SEQ ID NO 1
<211> LENGTH: 429
<212> TYPE: PRT
<213> ORGANISM: Artificial Sequence -continued

```
<220> FEATURE:
<223> OTHER INFORMATION: Description of Artificial Sequence: orfZ
      gene from C. kluyveri

<400> SEQUENCE: 1
```

Met Glu Trp Glu Glu Ile Tyr Lys Glu Lys Leu Val Thr Ala Glu Lys
 1               5                  10                  15

Ala Val Ser Lys Ile Glu Asn His Ser Arg Val Val Phe Ala His Ala
             20                  25                  30

Val Gly Glu Pro Val Asp Leu Val Asn Ala Leu Val Lys Asn Lys Asp
         35                  40                  45

Asn Tyr Ile Gly Leu Glu Ile Val His Met Val Ala Met Gly Lys Gly
     50                  55                  60

Val Tyr Thr Lys Glu Gly Met Gln Arg His Phe Arg His Asn Ala Leu
 65                  70                  75                  80

Phe Val Gly Gly Ser Thr Arg Asp Ala Val Asn Ser Gly Arg Ala Val
                 85                  90                  95

Tyr Thr Pro Cys Phe Phe Tyr Glu Val Pro Ser Leu Phe Lys Glu Lys
            100                 105                 110

Arg Leu Pro Val Asp Val Ala Leu Ile Gln Val Ser Glu Pro Asp Lys
        115                 120                 125

Tyr Gly Tyr Cys Ser Phe Gly Val Ser Asn Asp Tyr Thr Lys Pro Ala
    130                 135                 140

Ala Glu Ser Ala Lys Leu Val Ile Ala Glu Val Asn Lys Asn Met Pro
145                 150                 155                 160

Arg Thr Leu Gly Asp Ser Phe Ile His Val Ser Asp Ile Asp Tyr Ile
                165                 170                 175

Val Glu Ala Ser His Pro Leu Leu Glu Leu Gln Pro Pro Lys Leu Gly
            180                 185                 190

Asp Val Glu Lys Ala Ile Gly Glu Asn Cys Ala Ser Leu Ile Glu Asp
        195                 200                 205

Gly Ala Thr Leu Gln Leu Gly Ile Gly Ala Ile Pro Asp Ala Val Leu
    210                 215                 220

Leu Phe Leu Lys Asn Lys Lys Asn Leu Gly Ile His Ser Glu Met Ile
225                 230                 235                 240

Ser Asp Gly Val Met Glu Leu Val Lys Ala Gly Val Ile Asn Asn Lys
                245                 250                 255

Lys Lys Thr Leu His Pro Gly Lys Ile Val Val Thr Phe Leu Met Gly
            260                 265                 270

Thr Lys Lys Leu Tyr Asp Phe Val Asn Asn Asn Pro Met Val Glu Thr
        275                 280                 285

Tyr Ser Val Asp Tyr Val Asn Asn Pro Leu Val Ile Met Lys Asn Asp
    290                 295                 300

Asn Met Val Ser Ile Asn Ser Cys Val Gln Val Asp Leu Met Gly Gln
305                 310                 315                 320

Val Cys Ser Glu Ser Ile Gly Leu Lys Gln Ile Ser Gly Val Gly Gly
                325                 330                 335

Gln Val Asp Phe Ile Arg Gly Ala Asn Leu Ser Lys Gly Gly Lys Ala
            340                 345                 350

Ile Ile Ala Ile Pro Ser Thr Ala Gly Lys Gly Lys Val Ser Arg Ile
        355                 360                 365

Thr Pro Leu Leu Asp Thr Gly Ala Ala Val Thr Thr Ser Arg Asn Glu
    370                 375                 380

Val Asp Tyr Val Val Thr Glu Tyr Gly Val Ala His Leu Lys Gly Lys

```
385                 390                 395                 400
Thr Leu Arg Asn Arg Ala Arg Ala Leu Ile Asn Ile Ala His Pro Lys
                405                 410                 415

Phe Arg Glu Ser Leu Met Asn Glu Phe Lys Lys Arg Phe
        420                 425

<210> SEQ ID NO 2
<211> LENGTH: 52
<212> TYPE: PRT
<213> ORGANISM: Artificial Sequence
<220> FEATURE:
<223> OTHER INFORMATION: Description of Artificial Sequence:
      4-hydroxybutyryl CoA transferase (4HBCT) from C.
      aminobutyricum

<400> SEQUENCE: 2

Met Asp Trp Lys Lys Ile Tyr Glu Asp Arg Thr Ala Ile Ile Ala Met
 1               5                  10                  15

Pro Ser Val Ala Lys Asn Asp Ala Asp Tyr Val Val Thr Glu Tyr Gly
            20                  25                  30

Ile Ala Glu Met Lys Ala Leu Ile Asn Ile Ala His Pro Asp Phe Lys
        35                  40                  45

Asp Glu Leu Lys
    50

<210> SEQ ID NO 3
<211> LENGTH: 1289
<212> TYPE: DNA
<213> ORGANISM: Artificial Sequence
<220> FEATURE:
<223> OTHER INFORMATION: Description of Artificial Sequence: orzf
      gene from C. kluyveri

<400> SEQUENCE: 3
atggagtggg aagagatata taagagaaa ctggtaactg cagaaaaagc tgtttcaaaa       60
atagaaaacc atagcagggt agttttgca catgcagtag agaacccgt agatttagta      120 aatgcactag ttaaaaataa ggataattat ataggactag aaatagttca catggtagct     180
atgggcaaag gtgtatatac aaaagagggt atgcaaagac attttagaca taatgctttg     240
tttgtaggcg gatctactag agatgcagta aattcaggaa gagcagttta tacaccttgt     300
tttttctatg aagtgccaag tttgtttaaa gaaaaacgtt tgcctgtaga gtagcacttt     360
attcaggtaa gtgagccaga taaatatggc tactgcagtt ttggagtttc caatgactat     420
accaagccag cagcagaaag tgctaagctt gtaattgcag aagtgaataa aaacatgcca     480
agaactcttg gagattcttt tatacatgta tcagatattg attatatagt ggaagcttca     540
cacccattgt tagaattgca gcctcctaaa ttgggagatg tagaaaaagc cataggagaa     600
aactgtgcat ctttaattga agatggagct actcttcagc ttggaatagg tgctatacca     660
gatgcggtac ttttattctt aaagaacaaa agaatttag gaatacattc tgagatgata     720
tcagatggtg tgatggaact ggtgaaggca ggggttatca ataacaagaa aaagaccctc     780
catccaggca aatagttgt aacatttta atgggaacaa aaaattata tgattttgta     840 aacaataatc caatggtaga aacttattct gtagattatg taaataatcc actggtaatt     900
atgaaaaatg acaatatggt ttcaataaat tcttgtgttc aagtagactt aatgggacaa     960
gtatgttctg aaagtatagg attgaaacag taagtggag tggaggcca ggtagatttt    1020 attagaggag ctaatctatc aaagggtgga aaggctatta tagctatacc ttccacagct    1080
```

```
ggaaaaggaa aagtttcaag aataactcca cttctagata ctggtgctgc agttacaact      1140
tctagaaatg aagtagatta tgtagttact gaatatggtg ttgctcatct taagggcaaa      1200
ctttaagaaa tagggcaaga gctctaataa atatcgctca tccaaaattc agagaatcat      1260
taatgaatga atttaaaaag agattttag                                        1289
```

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence:
    oligonucleotide

<400> SEQUENCE: 4

```
aggaggtttt tatg                                                        14
```

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence:
    oligonucleotide

<400> SEQUENCE: 5

```
ggctcgtata atgtgtggag ggagaaccgc cgggctcgcg ccgtt                      45
```

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence:
    oligonucleotide

<400> SEQUENCE: 6

```
ctagaacggc gcgagcccgg cggttctccc tccacacatt atacgagcct gca             53
```

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:
    oligonucleotide

<400> SEQUENCE: 7

```
tcccctgtca taaagttgtc actgca                                           26
```

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:
    oligonucleotide

<400> SEQUENCE: 8

```
gtgacaactt tatgacaggg gatgca                                           26
```

<210> SEQ ID NO 9
<211> LENGTH: 58
<212> TYPE: DNA
<213> ORGANISM: Artificial Sequence
<220> FEATURE:

<223> OTHER INFORMATION: Description of Artificial Sequence:
      oligonucleotide

<400> SEQUENCE: 9
ctagtgccgg acccggttcc aaggccggcc gcaaggctgc agaactgag gaagcaca         58

<210> SEQ ID NO 10
<211> LENGTH: 56
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
tatgtgcttc ctcagttctg gcagccttgc ggccggcctt ggaaccgggt ccggca          56

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 11
ctctgaattc aaggaggaaa aaatatgaag ttattaaaat tggc                       44

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 12
tttctctgag ctcgggatat ttaatgattg tagg                                  34

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 13
aacgaattca attcaggagg tttttatgga tcagacatat tctctggagt c               51

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 14
ttgggagctc tacagtaaga aatgccgttg g                                     31

<210> SEQ ID NO 15
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 15
taagagctca attcaggagg tttttatgga taagaagcaa gtaacggatt taagg           55

```
<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 16 ttcccggggtt atcaggtatg cttgaagctg ttctgttggg c                          41

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 17
tccggatcca attcaggagg tttttatgaa cagcaataaa gagttaatgc ag              52

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 18
gattctagat aggagcggcg ctactgcttc gcc                                   33
```